(12) United States Patent
Miller et al.

(10) Patent No.: US 9,011,520 B2
(45) Date of Patent: Apr. 21, 2015

(54) TISSUE ANCHOR FOR ANNULOPLASTY DEVICE

(75) Inventors: Eran Miller, Moshav Beit Elazari (IL); Oz Cabiri, Macabim-Reut (IL)

(73) Assignee: Valtech Cardio, Ltd., Or Yehuda (IL)

( * ) Notice: Subject to any disclaimer, the term of this patent is extended or adjusted under 35 U.S.C. 154(b) by 456 days.

(21) Appl. No.: 13/504,870

(22) PCT Filed: Oct. 28, 2010

(86) PCT No.: PCT/IL2010/000890
§ 371 (c)(1),
(2), (4) Date: Jul. 19, 2012

(87) PCT Pub. No.: WO2011/051942
PCT Pub. Date: May 5, 2011

(65) Prior Publication Data
US 2012/0283757 A1    Nov. 8, 2012

Related U.S. Application Data

(63) Continuation-in-part of application No. 12/608,316, filed on Oct. 29, 2009, now Pat. No. 8,277,502.

(51) Int. Cl.
*A61F 2/24* (2006.01)
*A61B 17/04* (2006.01)
(Continued)

(52) U.S. Cl.
CPC .......... *A61F 2/2445* (2013.01); *A61B 17/0401* (2013.01); *A61B 17/064* (2013.01);
(Continued)

(58) Field of Classification Search
CPC .... A61F 2/2448; A61F 2/2445; A61F 2/2409

USPC ................. 623/2.1–2.19, 2.35–2.41
See application file for complete search history.

(56) References Cited

U.S. PATENT DOCUMENTS

| | | |
|---|---|---|
| 3,604,488 A | 9/1971 | Wishart et al. |
| 4,042,979 A | 8/1977 | Angell |

(Continued)

FOREIGN PATENT DOCUMENTS

| | | |
|---|---|---|
| WO | 92/05093 | 4/1992 |
| WO | 01/26586 | 4/2001 |

(Continued)

OTHER PUBLICATIONS

An International Search Report and a Written Opinion both dated May 19, 2011, which issued during the prosecution of Applicant's PCT/IL11/00064.

(Continued)

*Primary Examiner* — Jason-Dennis Stewart
(74) *Attorney, Agent, or Firm* — Sughrue Mion, PLLC

(57) ABSTRACT

Apparatus for use with an implant configured to be coupled to cardiac tissue of a patient, the apparatus including: a tissue anchor including: a distal tissue coupling element configured to couple the tissue anchor to the cardiac tissue of the patient, and a proximal implant-receiving element configured to receive at least a portion of the implant and facilitate coupling of the implant to the tissue anchor. The proximal implant-receiving element includes an implant-restraining element coupled to a portion of the implant-receiving element, the implant-restraining element being configured to restrain the implant from separating from the implant-receiving element. Other applications are also described.

27 Claims, 20 Drawing Sheets

(51) Int. Cl.
*A61B 17/064* (2006.01)
*A61B 17/068* (2006.01)

(52) U.S. Cl.
CPC ....... *A61B17/068* (2013.01); *A61B 2017/0409* (2013.01); *A61B 2017/0414* (2013.01); *A61B 2017/0427* (2013.01); *A61B 2017/0441* (2013.01); *A61B 2017/0448* (2013.01); *A61B 2017/0464* (2013.01); *A61B 2017/0647* (2013.01); *A61B 2017/0649* (2013.01); *A61F 2/2466* (2013.01)

(56) References Cited

U.S. PATENT DOCUMENTS

| | | | |
|---|---|---|---|
| 4,118,805 | A | 10/1978 | Reimels |
| 4,434,828 | A | 3/1984 | Trincia |
| 4,602,911 | A | 7/1986 | Ahmadi et al. |
| 4,625,727 | A | 12/1986 | Leiboff |
| 4,712,549 | A | 12/1987 | Peters |
| 4,778,468 | A | 10/1988 | Hunt et al. |
| 4,917,698 | A | 4/1990 | Carpenter et al. |
| 5,061,277 | A | 10/1991 | Carpentier et al. |
| 5,104,407 | A | 4/1992 | Lam et al. |
| 5,108,420 | A | 4/1992 | Marks |
| 5,306,296 | A | 4/1994 | Wright |
| 5,450,860 | A | 9/1995 | O'Connor |
| 5,477,856 | A | 12/1995 | Lundquist |
| 5,669,919 | A | 9/1997 | Sanders et al. |
| 5,674,279 | A | 10/1997 | Wright et al. |
| 5,810,882 | A | 9/1998 | Bolduc |
| 5,843,120 | A | 12/1998 | Israel et al. |
| 5,876,373 | A | 3/1999 | Giba et al. |
| 5,957,953 | A | 9/1999 | DiPoto |
| 5,961,440 | A | 10/1999 | Schweich et al. |
| 5,961,539 | A | 10/1999 | Northrup, III et al. |
| 6,045,497 | A | 4/2000 | Schweich et al. |
| 6,050,936 | A | 4/2000 | Schweich et al. |
| 6,059,715 | A | 5/2000 | Schweich et al. |
| 6,110,200 | A | 8/2000 | Hinnenkamp |
| 6,143,024 | A | 11/2000 | Campbell |
| 6,165,119 | A | 12/2000 | Schweich et al. |
| 6,183,411 | B1 | 2/2001 | Mortier |
| 6,187,040 | B1 | 2/2001 | Wright |
| 6,231,602 | B1 | 5/2001 | Carpentier |
| 6,251,092 | B1 | 6/2001 | Qin et al. |
| 6,319,281 | B1 | 11/2001 | Patel |
| 6,332,893 | B1 | 12/2001 | Mortier et al. |
| 6,402,780 | B2 | 6/2002 | Williamson, IV |
| 6,406,420 | B1 | 6/2002 | McCarthy et al. |
| 6,419,696 | B1 | 7/2002 | Ortiz |
| 6,451,054 | B1 | 9/2002 | Stevens |
| 6,470,892 | B1 | 10/2002 | Forsell |
| 6,524,338 | B1 | 2/2003 | Gundry |
| 6,537,314 | B2 | 3/2003 | Langberg et al. |
| 6,547,801 | B1 | 4/2003 | Dargent |
| 6,564,805 | B2 | 5/2003 | Garrison et al. |
| 6,569,198 | B1 | 5/2003 | Wilson |
| 6,589,160 | B2 | 7/2003 | Schweich et al. |
| 6,602,288 | B1 | 8/2003 | Cosgrove |
| 6,602,289 | B1 | 8/2003 | Colvin et al. |
| 6,613,078 | B1 | 9/2003 | Barone |
| 6,613,079 | B1 | 9/2003 | Wolinsky et al. |
| 6,619,291 | B2 | 9/2003 | Hlavka |
| 6,626,899 | B2 | 9/2003 | Houser et al. |
| 6,626,930 | B1 | 9/2003 | Allen et al. |
| 6,629,534 | B1 | 10/2003 | St. Goar et al. |
| 6,629,921 | B1 | 10/2003 | Schweich, Jr. et al. |
| 6,651,671 | B1 | 11/2003 | Donlon et al. |
| 6,652,556 | B1 | 11/2003 | VanTassel |
| 6,682,558 | B2 | 1/2004 | Tu et al. |
| 6,689,164 | B1 | 2/2004 | Seguin |
| 6,695,866 | B1 | 2/2004 | Kuehn et al. |
| 6,702,826 | B2 | 3/2004 | Liddicoat et al. |
| 6,702,846 | B2 | 3/2004 | Mikus et al. |
| 6,718,985 | B2 | 4/2004 | Hlavka et al. |
| 6,723,038 | B1 | 4/2004 | Schroeder et al. |
| 6,726,716 | B2 | 4/2004 | Marquez |
| 6,726,717 | B2 | 4/2004 | Alfieri et al. |
| 6,749,630 | B2 | 6/2004 | McCarthy et al. |
| 6,752,813 | B2 | 6/2004 | Goldfarb et al. |
| 6,764,510 | B2 | 7/2004 | Vidlund et al. |
| 6,786,924 | B2 | 9/2004 | Ryan et al. |
| 6,797,002 | B2 | 9/2004 | Spence et al. |
| 6,802,319 | B2 | 10/2004 | Stevens et al. |
| 6,805,710 | B2 | 10/2004 | Bolling et al. |
| 6,858,039 | B2 | 2/2005 | McCarthy |
| 6,884,250 | B2 | 4/2005 | Monassevitch et al. |
| 6,893,459 | B1 | 5/2005 | Macoviak |
| 6,908,482 | B2 | 6/2005 | McCarthy et al. |
| 6,986,775 | B2 | 1/2006 | Morales et al. |
| 6,989,028 | B2 | 1/2006 | Lashinski et al. |
| 7,004,176 | B2 | 2/2006 | Lau |
| 7,011,669 | B2 | 3/2006 | Kimblad |
| 7,011,682 | B2 | 3/2006 | Lashinski et al. |
| 7,037,334 | B1 | 5/2006 | Hlavka et al. |
| 7,077,862 | B2 | 7/2006 | Vidlund |
| 7,101,395 | B2 | 9/2006 | Tremulis et al. |
| 7,112,207 | B2 | 9/2006 | Allen et al. |
| 7,125,421 | B2 | 10/2006 | Tremulis et al. |
| 7,159,593 | B2 | 1/2007 | McCarthy et al. |
| 7,169,187 | B2 | 1/2007 | Datta et al. |
| 7,175,660 | B2 | 2/2007 | Cartledge et al. |
| 7,186,262 | B2 | 3/2007 | Saadat |
| 7,189,199 | B2 | 3/2007 | McCarthy et al. |
| 7,226,467 | B2 | 6/2007 | Lucatero et al. |
| 7,238,191 | B2 | 7/2007 | Bachmann |
| 7,294,148 | B2 | 11/2007 | McCarthy |
| 7,297,150 | B2 | 11/2007 | Cartledge et al. |
| 7,311,728 | B2 | 12/2007 | Solem et al. |
| 7,316,710 | B1 | 1/2008 | Cheng et al. |
| 7,329,280 | B2 | 2/2008 | Bolling et al. |
| 7,390,329 | B2 | 6/2008 | Westra et al. |
| 7,404,824 | B1 | 7/2008 | Webler et al. |
| 7,431,692 | B2 | 10/2008 | Zollinger |
| 7,452,376 | B2 | 11/2008 | Lim et al. |
| 7,455,690 | B2 | 11/2008 | Cartledge et al. |
| 7,507,252 | B2 | 3/2009 | Lashinski et al. |
| 7,530,995 | B2 | 5/2009 | Quijano et al. |
| 7,549,983 | B2 | 6/2009 | Roue et al. |
| 7,563,267 | B2 | 7/2009 | Goldfarb et al. |
| 7,563,273 | B2 | 7/2009 | Goldfarb et al. |
| 7,588,582 | B2 | 9/2009 | Starksen et al. |
| 7,604,646 | B2 | 10/2009 | Goldfarb et al. |
| 7,608,091 | B2 | 10/2009 | Goldfarb et al. |
| 7,608,103 | B2 | 10/2009 | McCarthy |
| 7,618,449 | B2 | 11/2009 | Tremulis et al. |
| 7,632,303 | B1 | 12/2009 | Stalker et al. |
| 7,635,329 | B2 | 12/2009 | Goldfarb et al. |
| 7,635,386 | B1 | 12/2009 | Gammie |
| 7,655,015 | B2 | 2/2010 | Goldfarb et al. |
| 7,992,567 | B2 | 8/2011 | Hirotsuka |
| 7,993,368 | B2 | 8/2011 | Gambale et al. |
| 8,123,800 | B2 | 2/2012 | McCarthy |
| 8,142,495 | B2 | 3/2012 | Hasenkam |
| 8,147,542 | B2 | 4/2012 | Maisano |
| 8,152,844 | B2 | 4/2012 | Rao |
| 8,226,711 | B2 | 7/2012 | Mortier |
| 8,241,351 | B2 | 8/2012 | Cabiri |
| 8,252,050 | B2 | 8/2012 | Maisano |
| 8,277,502 | B2 | 10/2012 | Miller |
| 8,287,591 | B2 | 10/2012 | Keidar |
| 8,353,956 | B2 | 1/2013 | Miller |
| 2001/0044656 | A1 | 11/2001 | Williamson |
| 2002/0042621 | A1 | 4/2002 | Liddicoat |
| 2002/0087048 | A1 | 7/2002 | Brock et al. |
| 2002/0103532 | A1 | 8/2002 | Langberg et al. |
| 2002/0173841 | A1 | 11/2002 | Ortiz et al. |
| 2002/0177904 | A1 | 11/2002 | Huxel et al. |
| 2003/0050693 | A1 | 3/2003 | Quijano et al. |
| 2003/0105519 | A1 | 6/2003 | Fasol |
| 2003/0167062 | A1 | 9/2003 | Gambale et al. |

(56) References Cited

U.S. PATENT DOCUMENTS

| | | |
|---|---|---|
| 2003/0199974 A1 | 10/2003 | Lee et al. |
| 2003/0204195 A1 | 10/2003 | Keane |
| 2003/0229350 A1 | 12/2003 | Kay |
| 2003/0229395 A1 | 12/2003 | Cox |
| 2003/0233142 A1 | 12/2003 | Morales et al. |
| 2004/0024451 A1 | 2/2004 | Johnson et al. |
| 2004/0049207 A1 | 3/2004 | Goldfarb |
| 2004/0092962 A1 | 5/2004 | Thornton et al. |
| 2004/0122514 A1 | 6/2004 | Fogarty et al. |
| 2004/0133274 A1 | 7/2004 | Webler |
| 2004/0148021 A1 | 7/2004 | Cartledge et al. |
| 2004/0172046 A1 | 9/2004 | Hlavka |
| 2004/0176788 A1 | 9/2004 | Opolski |
| 2004/0193191 A1 | 9/2004 | Starksen et al. |
| 2004/0236419 A1 | 11/2004 | Milo |
| 2005/0004668 A1 | 1/2005 | Aklog |
| 2005/0016560 A1 | 1/2005 | Voughlohn |
| 2005/0055087 A1 | 3/2005 | Starksen |
| 2005/0060030 A1 | 3/2005 | Lashinski |
| 2005/0065601 A1 | 3/2005 | Lee |
| 2005/0085903 A1 | 4/2005 | Lau |
| 2005/0090827 A1 | 4/2005 | Gedebou |
| 2005/0107871 A1 | 5/2005 | Realyvasquez |
| 2005/0125011 A1 | 6/2005 | Spence |
| 2005/0171601 A1 | 8/2005 | Cosgrove et al. |
| 2005/0177228 A1 | 8/2005 | Solem et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0288781 A1 | 12/2005 | Moaddeb et al. |
| 2006/0020326 A9 | 1/2006 | Bolduc et al. |
| 2006/0025787 A1 | 2/2006 | Morales et al. |
| 2006/0041319 A1 | 2/2006 | Taylor |
| 2006/0069429 A1 | 3/2006 | Spence et al. |
| 2006/0085012 A1 | 4/2006 | Dolan |
| 2006/0129166 A1 | 6/2006 | Lavelle |
| 2006/0161265 A1 | 7/2006 | Levine et al. |
| 2006/0241656 A1 | 10/2006 | Starksen et al. |
| 2006/0241748 A1 | 10/2006 | Lee et al. |
| 2006/0282161 A1 | 12/2006 | Huynh et al. |
| 2006/0287716 A1 | 12/2006 | Banbury et al. |
| 2007/0016287 A1 | 1/2007 | Cartledge |
| 2007/0016288 A1 | 1/2007 | Gurskis |
| 2007/0038221 A1 | 2/2007 | Fine |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0080188 A1 | 4/2007 | Spence |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0162111 A1 | 7/2007 | Fukamachi et al. |
| 2007/0198082 A1 | 8/2007 | Kapadia et al. |
| 2007/0213582 A1 | 9/2007 | Zollinger |
| 2007/0219558 A1 | 9/2007 | Deutsch |
| 2007/0250160 A1 | 10/2007 | Rafiee et al. |
| 2007/0255397 A1 | 11/2007 | Ryan |
| 2007/0255400 A1 | 11/2007 | Parravicini et al. |
| 2007/0282375 A1 | 12/2007 | Hindrichs et al. |
| 2007/0295172 A1 | 12/2007 | Swartz |
| 2008/0004697 A1 | 1/2008 | Lichtenstein |
| 2008/0027483 A1 | 1/2008 | Carledge |
| 2008/0035160 A1 | 2/2008 | Woodson et al. |
| 2008/0058595 A1 | 3/2008 | Snoke |
| 2008/0086203 A1 | 4/2008 | Roberts |
| 2008/0097523 A1 | 4/2008 | Bolduc et al. |
| 2008/0140116 A1 | 6/2008 | Bonutti |
| 2008/0167714 A1 | 7/2008 | St. Goar |
| 2008/0177382 A1 | 7/2008 | Hyde et al. |
| 2008/0195126 A1 | 8/2008 | Solem |
| 2008/0262609 A1 | 10/2008 | Gross |
| 2008/0275469 A1 | 11/2008 | Fanton |
| 2008/0281411 A1 | 11/2008 | Berreklouw |
| 2008/0288044 A1 | 11/2008 | Osborne |
| 2009/0043153 A1 | 2/2009 | Zollinger |
| 2009/0088837 A1 | 4/2009 | Gillinov et al. |
| 2009/0099650 A1 | 4/2009 | Bolduc et al. |
| 2009/0105816 A1 | 4/2009 | Olsen |
| 2009/0149872 A1 | 6/2009 | Gross et al. |
| 2009/0171439 A1 | 7/2009 | Nissl |
| 2009/0177266 A1 | 7/2009 | Powell et al. |
| 2009/0248148 A1 | 10/2009 | Shaolian |
| 2009/0259307 A1 | 10/2009 | Gross et al. |
| 2009/0287304 A1* | 11/2009 | Dahlgren et al. ............ 623/2.37 |
| 2009/0326648 A1 | 12/2009 | Machold et al. |
| 2010/0001038 A1 | 1/2010 | Levin |
| 2010/0010538 A1* | 1/2010 | Juravic et al. ................ 606/228 |
| 2010/0023117 A1 | 1/2010 | Yoganathan |
| 2010/0023118 A1 | 1/2010 | Medlock |
| 2010/0042147 A1 | 2/2010 | Janovsky |
| 2010/0130992 A1 | 5/2010 | Machold et al. |
| 2010/0152845 A1 | 6/2010 | Bloom |
| 2010/0161041 A1 | 6/2010 | Maisano et al. |
| 2010/0161042 A1 | 6/2010 | Maisano |
| 2010/0161043 A1 | 6/2010 | Maisano et al. |
| 2010/0161047 A1 | 6/2010 | Cabiri |
| 2010/0174358 A1 | 7/2010 | Rabkin et al. |
| 2010/0179574 A1 | 7/2010 | Longoria |
| 2010/0211166 A1 | 8/2010 | Miller et al. |
| 2010/0217382 A1* | 8/2010 | Chau et al. .................. 623/1.26 |
| 2010/0234935 A1 | 9/2010 | Bashiri et al. |
| 2010/0249920 A1 | 9/2010 | Bolling et al. |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0286628 A1 | 11/2010 | Gross |
| 2010/0286767 A1 | 11/2010 | Zipory et al. |
| 2010/0324598 A1 | 12/2010 | Anderson |
| 2011/0029066 A1 | 2/2011 | Gilad et al. |
| 2011/0082538 A1 | 4/2011 | Dahlgren |
| 2011/0087146 A1 | 4/2011 | Ryan et al. |
| 2011/0093002 A1 | 4/2011 | Rucker et al. |
| 2011/0106245 A1 | 5/2011 | Miller et al. |
| 2011/0106247 A1 | 5/2011 | Miller |
| 2011/0166649 A1 | 7/2011 | Gross et al. |
| 2011/0184510 A1 | 7/2011 | Maisano et al. |
| 2011/0190879 A1 | 8/2011 | Bobo et al. |
| 2011/0208283 A1 | 8/2011 | Rust |
| 2011/0238088 A1 | 9/2011 | Bolduc |
| 2011/0282361 A1 | 11/2011 | Miller et al. |
| 2011/0288635 A1 | 11/2011 | Miller et al. |
| 2011/0301698 A1 | 12/2011 | Miller |
| 2012/0022557 A1 | 1/2012 | Cabiri |
| 2012/0035712 A1 | 2/2012 | Maisano |
| 2012/0078355 A1 | 3/2012 | Zipory |
| 2012/0123531 A1 | 5/2012 | Tsukashima |
| 2012/0136436 A1 | 5/2012 | Cabiri |
| 2012/0330410 A1 | 12/2012 | Hammer |
| 2013/0116780 A1 | 5/2013 | Miller |

FOREIGN PATENT DOCUMENTS

| | | |
|---|---|---|
| WO | 02/085251 | 10/2002 |
| WO | 02/085252 | 10/2002 |
| WO | 2005/021063 | 3/2005 |
| WO | 2005/062931 | 7/2005 |
| WO | 2006/097931 | 9/2006 |
| WO | 2006/116558 | 11/2006 |
| WO | 2007/136783 | 11/2007 |
| WO | 2008/068756 | 6/2008 |
| WO | 2010/004546 | 1/2010 |
| WO | 2010/073246 | 7/2010 |
| WO | 2010/128502 | 11/2010 |
| WO | 2010/128503 | 11/2010 |
| WO | 2011/051942 | 5/2011 |

(56) References Cited

FOREIGN PATENT DOCUMENTS

| WO | 2011/089601 | 7/2011 |
|---|---|---|
| WO | 2011/154942 | 12/2011 |

OTHER PUBLICATIONS

Amplatzer Cardiac Plug brochure (English pages), AGA Medical Corporation (Plymouth, MN) (copyright 2008-2010, downloaded Jan. 11, 2011).

U.S. Appl. No. 60/902,146, filed Feb. 16, 2007.

Agarwal et al. International Cardiology Perspective Functional Tricuspid Regurgitation, Circ Cardiovasc Interv 2009;2;2;565-573 (2009).

An Office Action dated Oct. 6, 2010, which issued during the prosecution of Applicant's U.S. Appl. No. 12/484,512.

An Office Action dated Dec. 29, 2011, which issued during the prosecution of U.S. Appl. No. 12/563,952.

O'Reilly S et al., "Heart valve surgery pushes the envelope," Medtech Insight 8(3): 73, 99-108 (2006).

An International Search Report dated Feb. 2, 2012, which issued during the prosecution of Applicant's PCT/IL2011/000600.

An Office Action dated Sep. 28, 2011, which issued during the prosecution of U.S. Appl. No. 12/437,103.

An Office Action dated Mar. 9, 2012, which issued during the prosecution of U.S. Appl. No. 12/689,635.

An International Preliminary Report on Patentability dated Nov. 9, 2011, which issued during the prosecution of Applicant's PCT/IL2010/000358.

An International Search Report and a Written Opinion both dated Nov. 8, 2010, which issued during the prosecution of Applicant's PCT/IL2010/000358.

An International Search Report and a Written Opinion both dated Nov. 11, 2011, which issued during the prosecution of Applicant's PCT/IL2011/000404.

An International Search Report and a Written Opinion both dated Nov. 23, 2011, which issued during the prosecution of Applicant's PCT/IL2011/00446.

An Office Action dated Jan. 23, 2012, which issued during the prosecution of U.S. Appl. No. 12/692,061.

U.S. Appl. No. 60/873,075, filed Dec. 5, 2006.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Swain CP et al., "An endoscopically deliverable tissue-transfixing device for securing biosensors in the gastrointestinal tract," Gastrointestinal Endoscopy 40(6): 730-734 (1994).

An Office Action dated Jul. 6, 2012, which issued during the prosecution of U.S. Appl. No. 12/692,061.

Odell JA et al., "Early Results of a Simplified Method of Mitral Valve Annuloplasty," Circulation 92:150-154 (1995).

An International Search Report dated Sep. 8, 2009, which issued during the prosecution of Applicant's PCT/IL09/00593.

U.S. Appl. No. 61/001,013, filed Oct. 29, 2007.

U.S. Appl. No. 61/132,295, filed Jun. 16, 2008.

"Two dimensional real-time ultrasonic imaging of the heart and great vessels", Mayo Clin Proc. vol. 53:271-303, 1978.

An International Search Report dated Jun. 10, 2010, which issued during the prosecution of Applicant's PCT/IL09/01209.

An Office Action dated Mar. 29, 2011, which issued during the prosecution of U.S. Appl. No. 12/341,960.

An Interview Summary dated Jul. 27, 2011, which issued during the prosecution of U.S. Appl. No. 12/341,960.

An International Preliminary Report on Patentability dated Jun. 29, 2011, which issued during the prosecution of Applicant's PCT/IL2009/001209.

A Restriction Requirement dated Apr. 19, 2010, which issued during the prosecution of U.S. Appl. No. 12/341,960.

An International Search Report and a Written Opinion both dated Aug. 17, 2010, which issued during the prosecution of Applicant's PCT/IL10/00357.

An Office Action dated Aug. 4, 2010, which issued during the prosecution of U.S. Appl. No. 12/341,960.

Supplementary European Search Report dated Dec. 4, 2012, which issued during the prosecution of European Patent Application No. 09834225.

An Office Action dated Jan. 17, 2013, which issued during the prosecution of U.S. Appl. No. 13/167,444.

An Office Action dated Feb. 12, 2013, which issued during the prosecution of U.S. Appl. No. 12/926,673.

An Office Action dated Jan. 27, 2012, which issued during the prosecution of U.S. Appl. No. 12/548,991.

An Office Action dated Aug. 6, 2012, which issued during the prosecution of U.S. Appl. No. 12/548,991.

A Notice of Allowance dated May 24, 2012, which issued during the prosecution of U.S. Appl. No. 12/563,952.

An International Search Report and a Written Opinion both dated Feb. 10, 2011, which issued during the prosecution of Applicant's PCT/IL10/00890.

An International Preliminary Report on Patentability dated May 1, 2012, which issued during the prosecution of Applicant's PCT/IL10/00890.

An Office Action dated Jan. 17, 2013, which issued during the prosecution of U.S. Appl. No. 12/795,192.

An Office Action dated Jul. 20, 2012, which issued during the prosecution of U.S. Appl. No. 12/843,412.

An Office Action dated Mar. 27, 2013, which issued during the prosecution of U.S. Appl. No. 12/843,412.

A Notice of Allowance dated May 2, 2013, which issued during the prosecution of U.S. Appl. No. 12/843,412.

An Office Action dated May 10, 2012, which issued during the prosecution of U.S. Appl. No. 12/795,026.

An Office Action dated Nov. 5, 2012, which issued during the prosecution of U.S. Appl. No. 12/795,026.

A Restriction Requirement dated Feb. 4, 2013, which issued during the prosecution of U.S. Appl. No. 13/141,606.

A Notice of Allowance dated Apr. 27, 2012, which issued during the prosecution of U.S. Appl. No. 12/431,960.

A Restriction Requirement dated Apr. 1, 2011, which issued during the prosecution of U.S. Appl. No. 12/608,316.

An Office Action dated Nov. 14, 2011, which issued during the prosecution of U.S. Appl. No. 12/608,316.

A Notice of Allowance dated Jun. 26, 2012, which issued during the prosecution of U.S. Appl. No. 12/608,316.

Supplementary European Search Report dated Feb. 1, 2011, which issued during the prosecution of EP Patent Application No. 07849540.

An Office Action dated May 6, 2013, which issued during the prosecution of U.S. Appl. No. 12/689,693.

An Office Action dated Aug. 15, 2013, which issued during the prosecution of U.S. Appl. No. 12/795,192.

Dictionary.com definition of "lock", Jul. 29, 2013.

An Office Action dated Feb. 3, 2014 which issued during the prosecution of U.S. Appl. No. 12/689,693.

Search Report in European Patent Application 10772090.6 dated Jan. 17, 2014.

Supplementary European Search Report dated Jan. 21, 2014 which issued during the prosecution of Applicant's European App No. 11 78 6226.8.

International Search Report and Written Opinion, dated Mar. 21, 2014, issued by the International Searching Authority, in counterpart Application No. PCT/IL13/50992.

International Search Report and Written Opinion, dated Apr. 9, 2014, issued by the International Search Authority, in counterpart Application No. PCT/IL13/50860.

Notice of Allowance dated Nov. 19, 2013, which issued during the prosecution of U.S. Appl. No. 12/795,192.

An Office Action dated Dec. 16, 2013, which issued during the prosecution of U.S. Appl. No. 13/666,262.

An Office Action dated Dec. 27, 2013, which issued during the prosecution of U.S. Appl. No. 12/785,717.

(56) References Cited

OTHER PUBLICATIONS

An English translation of an Office Action dated Apr. 23, 2014 which issued during the prosecution of Chinese Patent Application No. 201080059948.4.
An Office Action dated Jun. 4, 2014, which issued during the prosecution of U.S. Appl. No. 12/840,463.
An Office Action dated Jun. 11, 2014, which issued during the prosecution of U.S. Appl. No. 14/027,934.
Notice of Allowance dated Jun. 11, 2014, which issued during the prosecution of U.S. Appl. No. 12/689,693.
Notice of Allowance dated Jun. 25, 2014, which issued during the prosecution of U.S. Appl. No. 13/666,262.
An Office Action dated Aug. 22 2014, which issued during the prosecution of U.S. Appl. No. 14/027,934.
An English translation of an Office Action dated Jul. 25, 2014 which issued during the prosecution of Chinese Patent Application No. 200980157331.3.
Notice of Allowance dated Aug. 26, 2014, which issued during the prosecution of U.S. Appl. No. 13/167,444.
Notice of Allowance dated Jun. 23, 2014, which issued during the prosecution of U.S. Appl. No. 12/548,991.
An Office Action dated Aug. 22, 2014, which issued during the prosecution of U.S. Appl. No. 14/027,934.
An Office Action dated Aug. 26, 2014, which issued during the prosecution of U.S. Appl. No. 13/167,444.
An Office Action dated Oct. 14, 2014, which issued during the prosecution of U.S. Appl. No. 13/319,030.
Communication dated Oct. 30, 2014, issued by the European Patent Office in counterpart European Application No. 10826224.7.

* cited by examiner

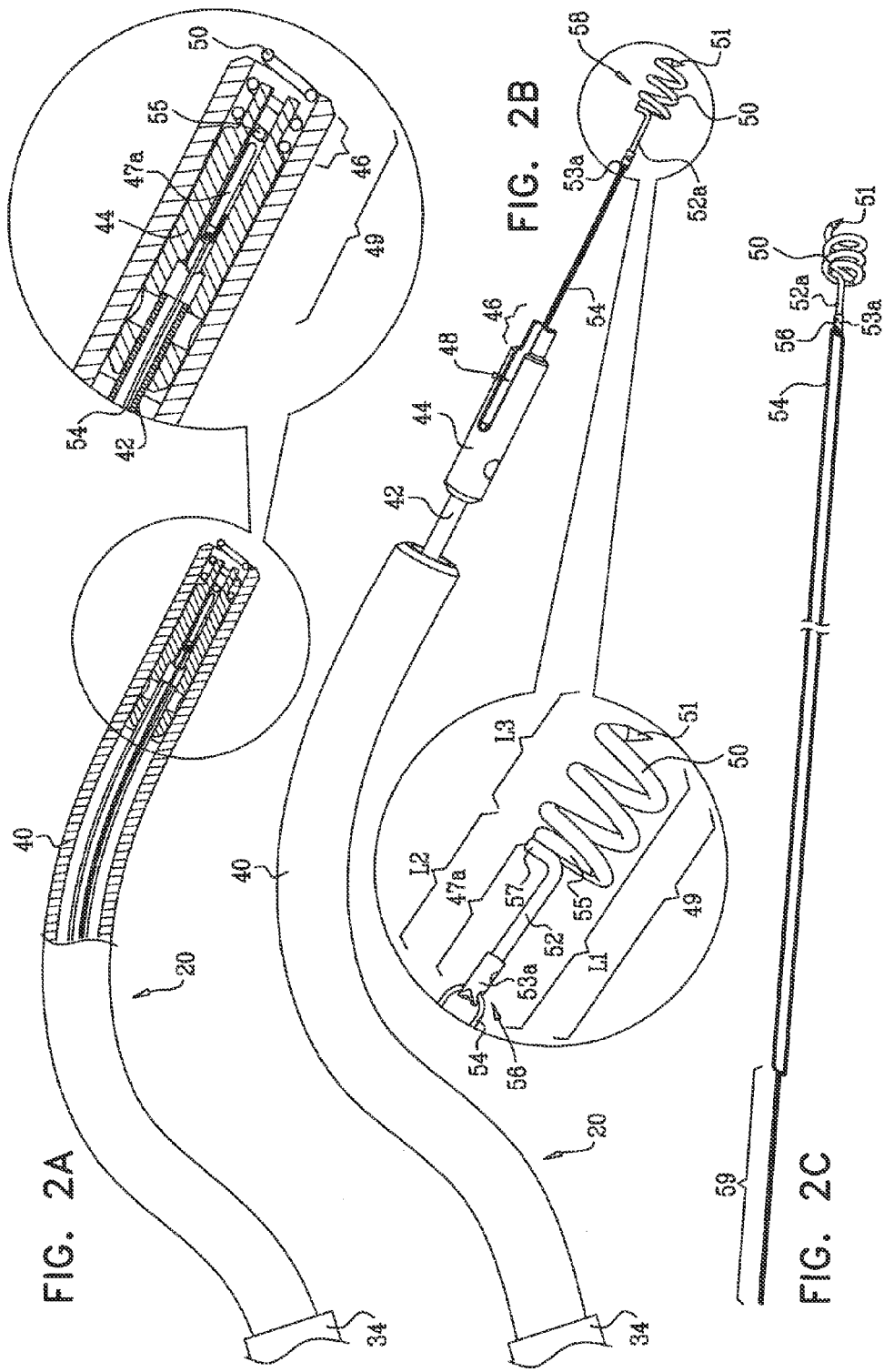

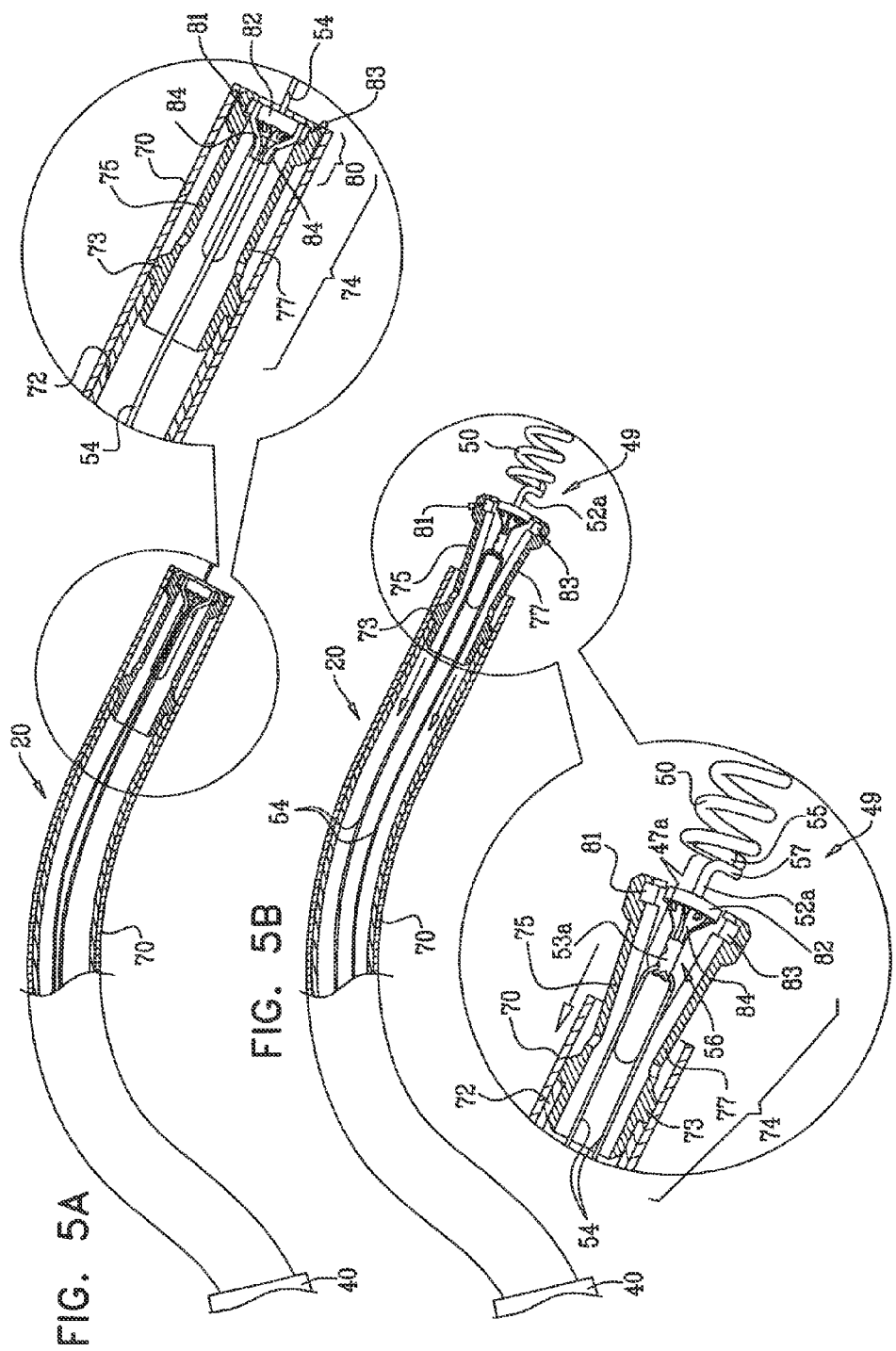

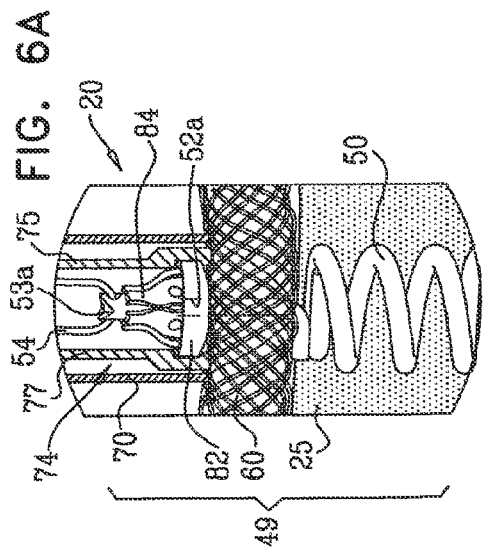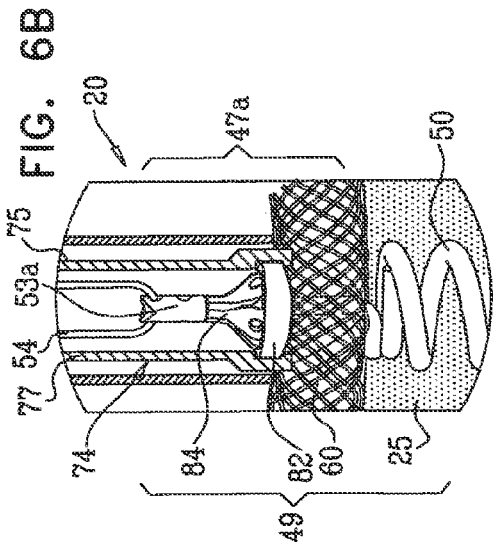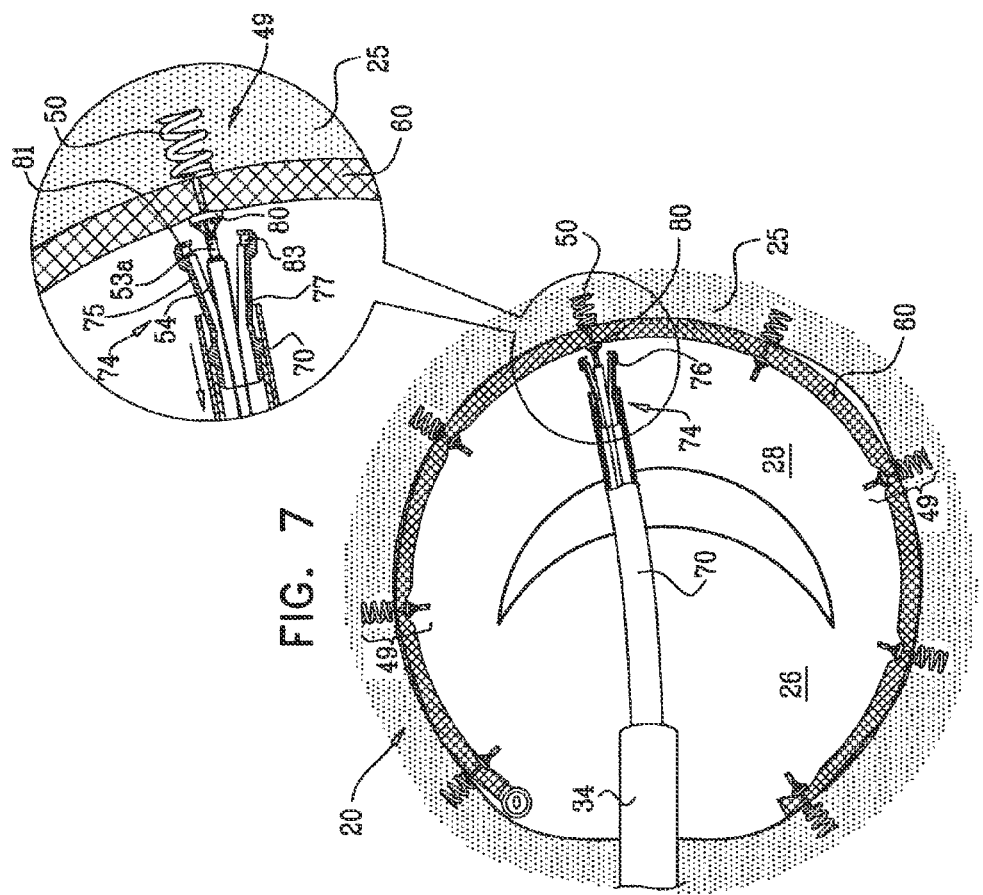

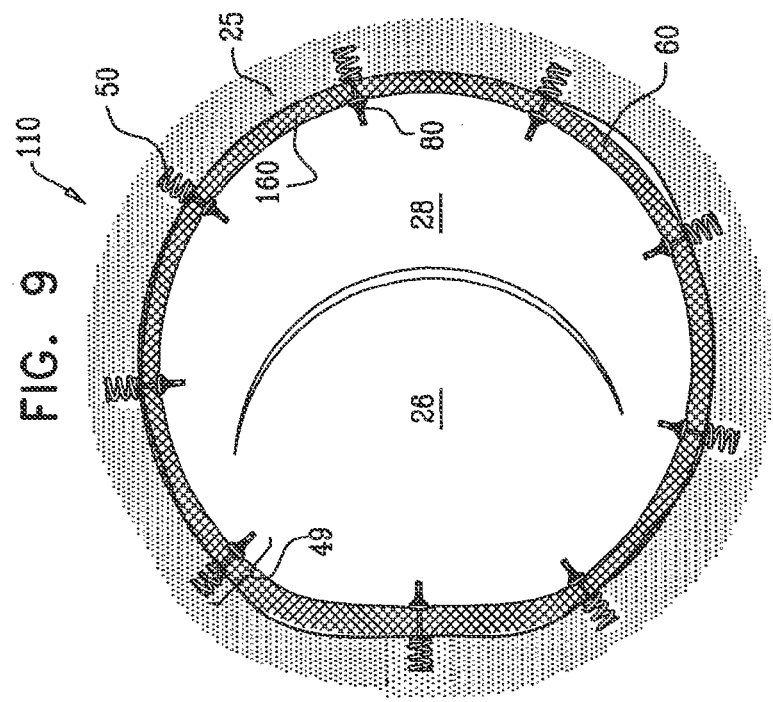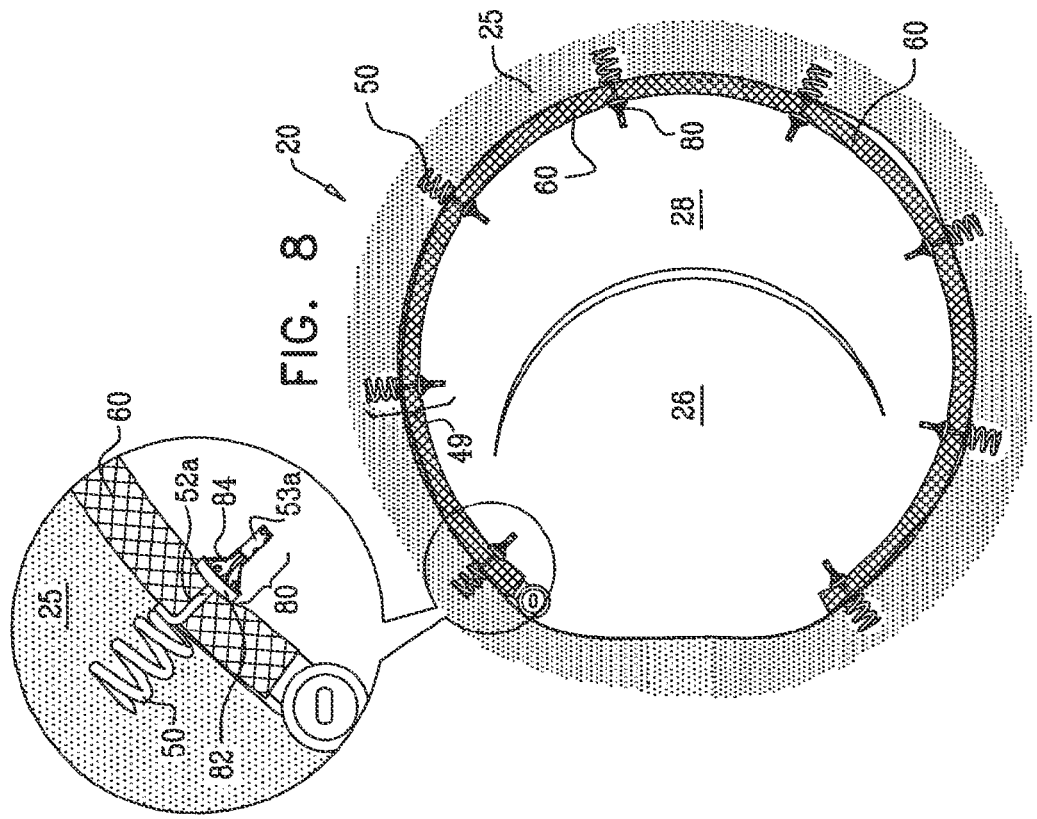

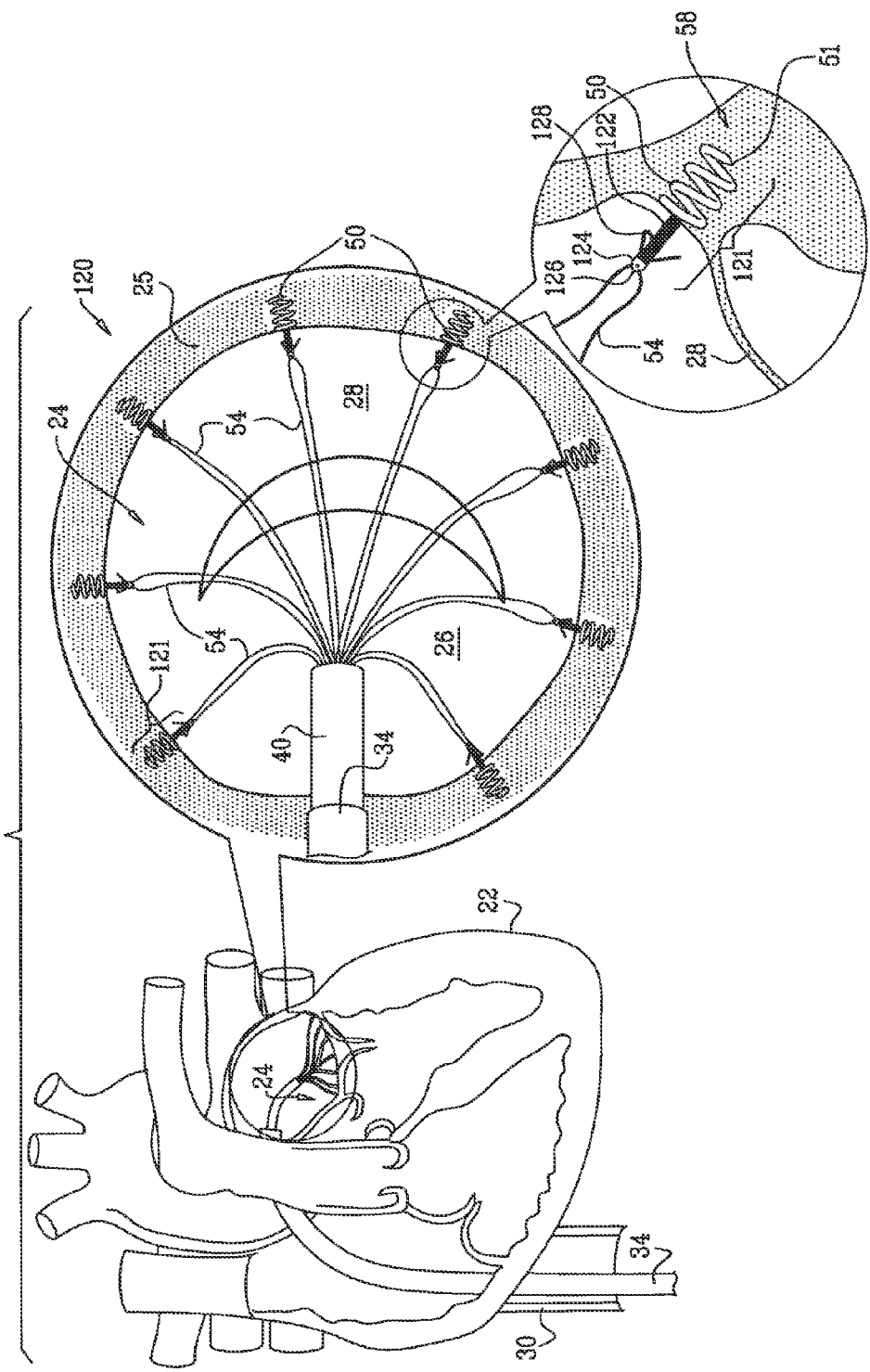

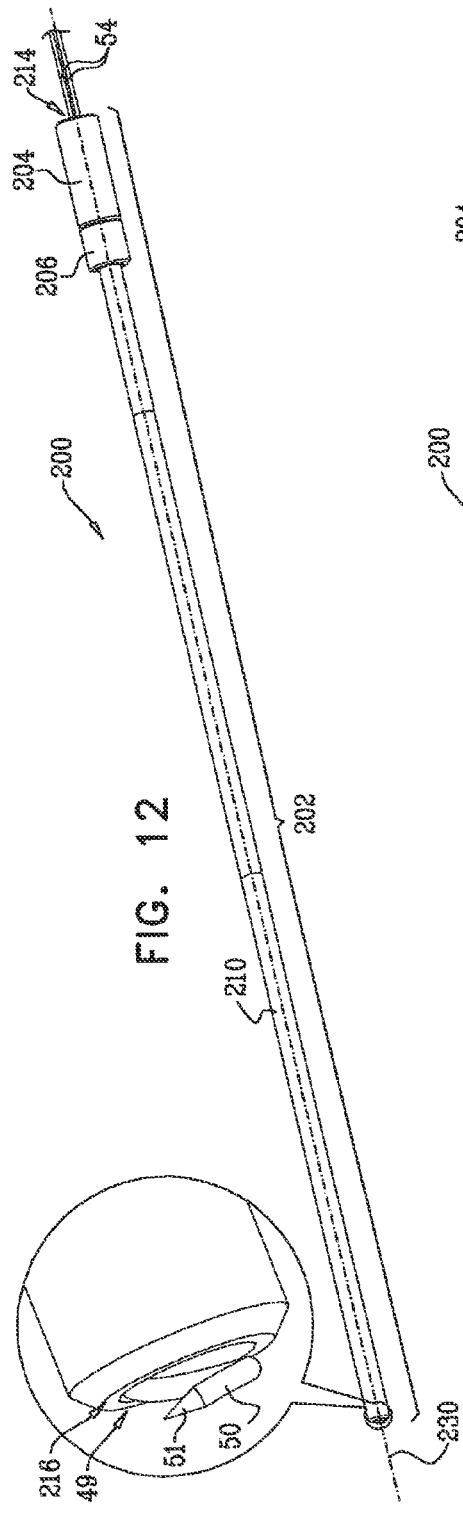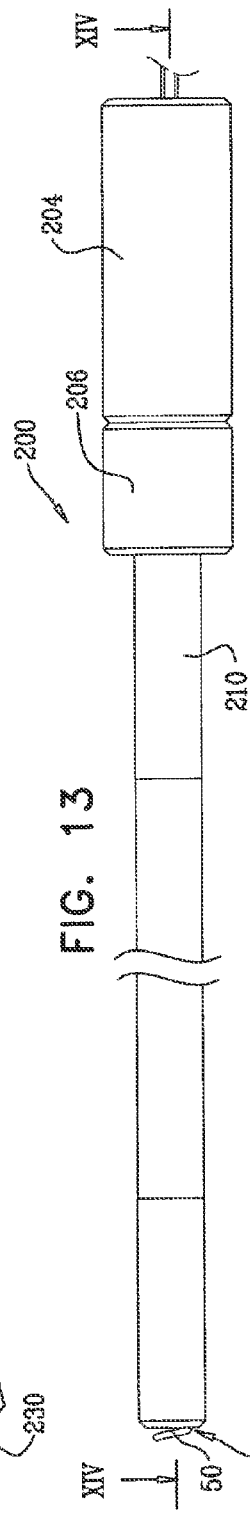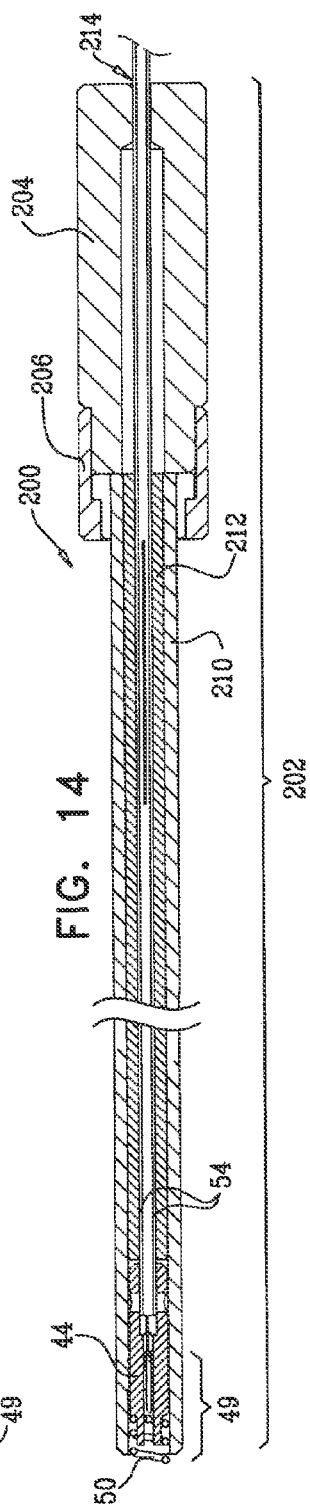

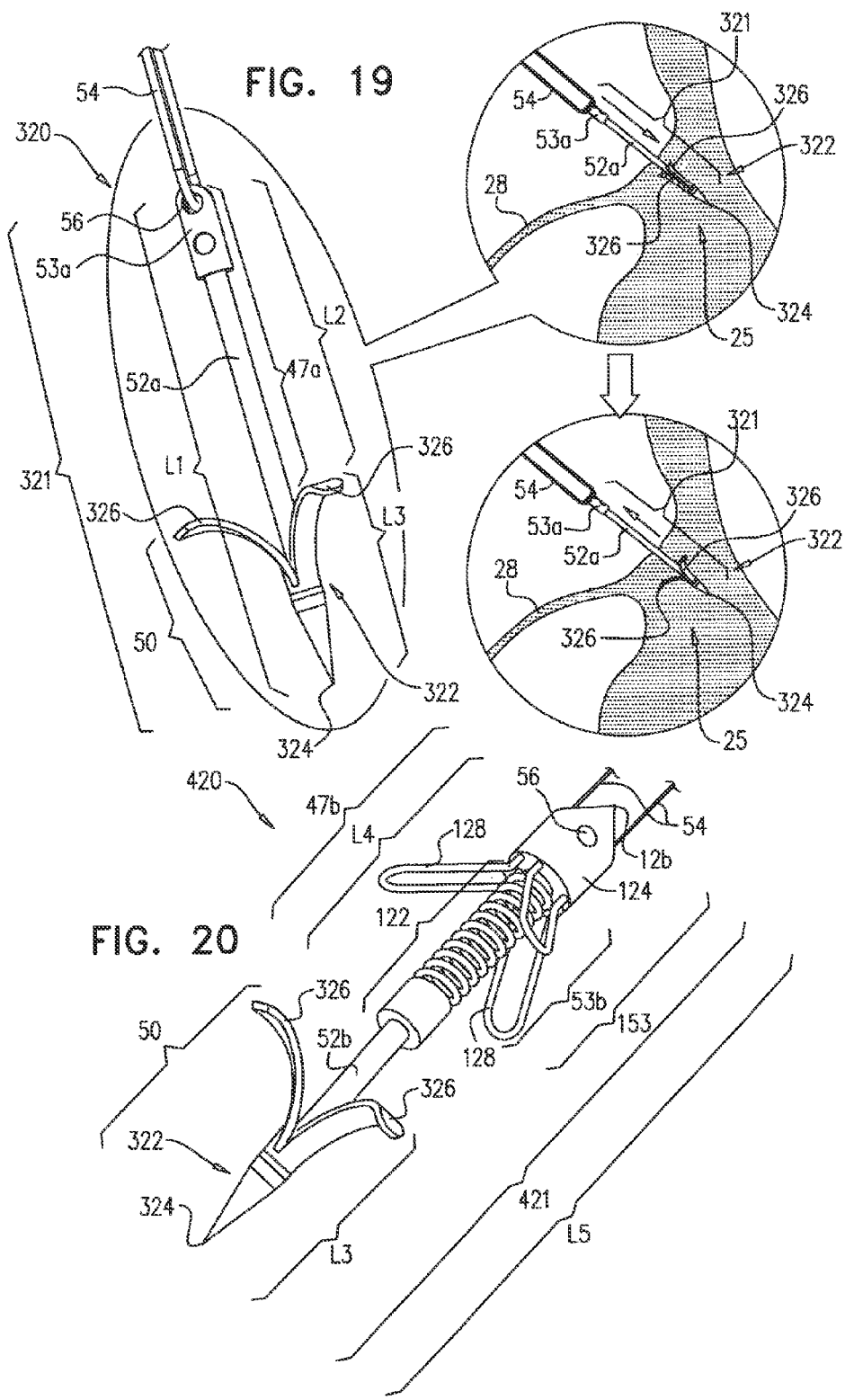

TISSUE ANCHOR FOR ANNULOPLASTY DEVICE

CROSS-REFERENCES TO RELATED APPLICATIONS

The present application is a US national phase application of PCT/IL2010/000890 to Miller et al., entitled, "Tissue anchor for annuloplasty device," filed on Oct. 28, 2010, which published as WO 2011/051942, and which claims priority from and is a continuation-in-part of U.S. patent application Ser. No. 12/608,316 to Miller et al., entitled, "Tissue anchor for annuloplasty device," filed on Oct. 29, 2009, which issued as U.S. Pat. No. 8,277,502. Both of these applications are incorporated herein by reference.

FIELD OF THE INVENTION

Some applications of the present invention relate in general to tissue anchors. More specifically, some applications of the present invention relate to tissue anchors for repair of an atrioventricular valve of a patient.

BACKGROUND OF THE INVENTION

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

US Patent Application 2004/0236419 to Milo describes methods for reconfiguring an atrioventricular heart valve that may use systems comprising a partial or complete annuloplasty rings proportioned to reconfigure a heart valve that has become in some way incompetent, a pair of trigonal sutures or implantable anchors, and a plurality of staples which may have pairs of legs that are sized and shaped for association with the ring at spaced locations along its length. These systems permit relative axial movement between the staples and the ring, whereby a patient's heart valve can be reconfigured in a manner that does not deter subtle shifting of the native valve components. Shape-memory alloy material staples may have legs with free ends that interlock following implantation. Annuloplasty rings may be complete or partial and may be fenestrated. One alternative method routes a flexible wire, preferably of shape-memory material, through the bights of pre-implanted staples. Other alternative systems use linkers of shape-memory material having hooked ends to interengage with staples or other implanted supports which, following implantation, decrease in effective length and pull the staples or other supports toward one another so as to create desired curvature of the reconfigured valve. These linkers may be separate from the supports or may be integral with them and may have a variety of shapes and forms. Various of these systems may be implanted non-invasively using a delivery catheter.

US 2007/0049942 to Hindrichs et al. describes remodeling a soft body tissue structure by shortening the distance between first and second portions of that tissue structure. First and second anchor structures are respectively implanted in the first and second portions of the tissue structure. These anchor structures are linked by a linking structure, the length of which between the anchor structures can be shortened to pull the tissue structure portions toward one another. Each of the anchor structures may include two screw structures that are driven into the associated tissue structure portion transverse to the linking structure and with a spacer between the two screws. The entire prosthesis can be implanted percutaneously if desired. An illustrative use of the prosthesis is to shorten the annulus of a patient's mitral valve, with at least a portion of the prosthesis implanted in the patient's coronary sinus.

The following patents and patent application publications may be of interest:
PCT Publication WO 07/136,783 to Cartledge et al.
PCT Publication WO 08/068,756 to Gross et al.
PCT Publication WO 10/004,546 to Gross et al.
PCT Publication WO 10/073,246 to Cabiri et al.
U.S. Pat. No. 5,306,296 to Wright et al.
U.S. Pat. No. 6,569,198 to Wilson et al.
U.S. Pat. No. 6,619,291 to Hlavka et al.
U.S. Pat. No. 6,764,510 to Vidlund et al.
U.S. Pat. No. 7,004,176 to Lau
U.S. Pat. No. 7,101,395 to Tremulis et al.
U.S. Pat. No. 7,175,660 to Cartledge et al.
US 2003/0050693 to Quijano et al
US 2003/0167062 to Gambale et al.
US 2004/0024451 to Johnson et al.
US 2004/0148021 to Cartledge et al.
US 2005/0171601 to Cosgrove et al.
US 2005/0288781 to Moaddeb et al.
US 2007/0016287 to Cartledge et al.
US 2007/0080188 to Spence et al.
US 2007/0219558 to Deutsch
US 2007/0282375 to Hindrichs et al.
US 2008/0262609 to Gross et al.
US 2010/0161041 to Maisano et al.
US 2010/0161042 to Maisano et al.
US 2010/0211166 to Miller et al.

The following articles may be of interest:
O'Reilly S et al., "Heart valve surgery pushes the envelope," Medtech Insight 8(3): 73, 99-108 (2006)
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003)

SUMMARY OF THE INVENTION

In some applications of the present invention, a tissue anchor is provided that is configured for receiving an implant and facilitating implantation of the implant. The anchor comprises a distal tissue coupling element, e.g., a helical anchor, which penetrates tissue of a patient. The anchor also comprises a proximal implant-penetrating element which receives and facilitates coupling of the implant to the tissue anchor. The implant-penetrating element comprises a post, which extends between the proximal tip and the proximal end of the distal tissue coupling element. For some applications, the proximal tip of the implant-penetrating element comprises a barb which punctures and receives the implant.

Typically, during an open-heart, minimally-invasive, or transcatheter procedure, a plurality of tissue anchors are implanted along an annulus of an atrioventricular valve of the patient, and are configured to receive and facilitate implantation of a valve-repair implant, e.g., an annuloplasty ring or a prosthetic valve. Each anchor is reversibly coupled to a cord, e.g., a suture or a wire, at a proximal end of the implant-penetrating element. Prior to implantation of the valve-repair implant, each cord is threaded through the implant, and the implant is then slid toward the annulus along the cords. In response to continued pushing of the valve-repair implant, the implant is then punctured at respective locations by the proximal tips of each one of the implant-penetrating elements. The physician continues to push the valve-repair implant so that the implant slides along the implant-penetrating elements and the posts of the anchors. The implant is pushed along the post until the proximal tips of each one of the implant-penetrating elements are exposed from within the lumen of the valve-repair implant and disposed proximally to a proximal surface of the implant. The valve-repair implant is then locked in place at the surface of the implant that faces the lumen of the atrium of the patient. Following the locking in place of the implant, the cords are decoupled from the anchors and removed from within the body of the patient.

In some applications of the present invention, a proximal restraining element, e.g., radially-expandable arms, is coupled to a proximal portion of the post of the anchor. This restraining element restrains the implant from separating from the implant-penetrating element.

In some applications of the present invention, an elastic portion, e.g., a tension spring, is coupled at a proximal end to the proximal tip of the implant-penetrating element, and at a distal end to the proximal end of the post.

There is therefore provided, in accordance with some applications of the present invention, apparatus for use with an implant, the apparatus including:
 a tissue anchor, which includes:
  a distal tissue coupling element, which is configured to penetrate cardiac tissue; and
  a proximal implant-penetrating element configured to penetrate the implant, the proximal implant-penetrating element being shaped so as to define a passage therethrough, which passage has at least two openings that are within 1 mm of a proximal end of the implant-penetrating element; and
 a cord configured to be removably passed through the passage.

In some applications of the present invention, the proximal implant-penetrating element includes a post.

In some applications of the present invention, the post has a length of between 1 and 7 mm and a greatest cross-sectional area of between 0.03 mm^2 and 0.2 mm^2, which length is at least 4 times the square root of the greatest cross-sectional area.

In some applications of the present invention, the length of the post is at least 5 times the square root of the greatest cross-sectional area of the post.

In some applications of the present invention, the length of the post is at least 8 times the square root of the greatest cross-sectional area of the post.

In some applications of the present invention, the length of the post is at least 10 times the square root of the greatest cross-sectional area of the post.

In some applications of the present invention, the length of the post is at least 15 times the square root of the greatest cross-sectional area of the post.

In some applications of the present invention, the apparatus further includes a proximal restraining element, which is configured to be coupleable to the post within 2 mm of a proximal end of the post, and which is configured to restrain the implant from separating from the implant-penetrating element.

In some applications of the present invention, the proximal restraining element is shaped so as to define an opening therethrough, through which the cord is configured to pass.

In some applications of the present invention, the post defines a protrusion configured to protrude into a plane of the implant and to couple the implant to the tissue anchor.

In some applications of the present invention, the protrusion is shaped so as to define a distal shelf that has a transverse cross-sectional length that is larger than a transverse cross-sectional length of the implant-receiving element, the distal shelf being configured to facilitate restricting of proximal motion of the implant along the protrusion.

In some applications of the present invention, the proximal restraining element has a greatest cross-sectional area that is at least 1.5 times a greatest cross-sectional area of the post.

In some applications of the present invention, the apparatus further includes a lock configured to be advanced toward the anchor and disposed between the implant and the proximal restraining element, the lock including:
 a distal portion configured to rest against the implant, and
 an expandable proximal portion having a cross-sectional area during a resting state of the lock that is larger than the greatest cross-sectional area of the post and smaller than the greatest cross-sectional area of the proximal restraining element.

In some applications of the present invention, the proximal implant-penetrating element includes a barb configured to restrict proximal movement of the implant along the implant-penetrating element.

In some applications of the present invention, the barb includes a proximal restraining element which is configured to restrain the implant from separating from the implant-penetrating element.

In some applications of the present invention, the barb includes one or more arms that are radially expandable to rest against an external surface of the implant following coupling of the implant to the implant-penetrating element.

In some applications of the present invention, the arms are radially collapsible during at least a portion of the coupling of the implant to the implant-penetrating element.

In some applications of the present invention, the proximal implant-penetrating element includes an elastic portion that is configured to assume a first length when relaxed, and a second, greater length when under load.

In some applications of the present invention, the elastic portion includes a tension spring.

In some applications of the present invention, the proximal implant-penetrating element has a length of between 3 and 5 mm when the elastic portion is relaxed.

In some applications of the present invention, the implant-penetrating element includes a proximal restraining element which is coupled to the post, and which is configured to restrain the implant from separating from the implant-penetrating element.

In some applications of the present invention, the proximal restraining element is coupled within 2 mm of a proximal end of the post.

In some applications of the present invention, the proximal restraining element is shaped so as to define an opening therethrough, through which the cord is configured to pass.

In some applications of the present invention, the proximal restraining element includes a protrusion configured to protrude into a plane of the implant and to couple the implant to the tissue anchor.

In some applications of the present invention, the protrusion is shaped so as to define a distal shelf that has a transverse cross-sectional length that is larger than a transverse cross-sectional length of the implant-receiving element, the distal shelf being configured to facilitate restricting of proximal motion of the implant along the protrusion.

In some applications of the present invention, the proximal restraining element has a greatest cross-sectional area that is at least 1.5 times a greatest cross-sectional area of the post.

In some applications of the present invention, the apparatus further includes a lock configured to be advanced toward the anchor and disposed between the implant and the proximal restraining element, the lock including:
 a distal portion configured to rest against the implant, and
 an expandable proximal portion having a cross-sectional area during a resting state of the lock that is larger than the greatest cross-sectional area of the post and smaller than the greatest cross-sectional area of the proximal restraining element.

I the proximal restraining element includes a barb configured to restrict proximal movement of the implant along the implant-penetrating element.

In some applications of the present invention, the barb includes one or more arms that are radially expandable to rest against an external surface of the implant following coupling of the implant to the implant-penetrating element.

In some applications of the present invention, the arms are radially collapsible during at least a portion of the coupling of the implant to the implant-penetrating element.

In some applications of the present invention, the proximal implant-penetrating element includes an elastic portion that is configured to assume a first length when relaxed, and a second, greater length when under load.

In some applications of the present invention, the elastic portion includes a tension spring.

In some applications of the present invention, the proximal implant-penetrating element has a length of between 3 and 5 mm when the elastic portion is relaxed.

In some applications of the present invention, the coupling element is shaped so as to define a shape selected from the group consisting of: a helix, a spiral, and a screw shaft.

In some applications of the present invention, the coupling element is shaped so as to define one or more radially-expandable prongs, the prongs being configured to expand and facilitate anchoring of the coupling element and restrict proximal motion of the tissue anchor.

In some applications of the present invention, the apparatus further includes the implant, the post is configured to couple the implant to the anchor.

In some applications of the present invention, the implant includes an annuloplasty device.

In some applications of the present invention, the annuloplasty device includes:
 a sleeve having a lumen;
 a spool coupled to the sleeve; and
 a flexible contracting member that is coupled to the spool and the sleeve, such that winding the contracting member around the spool tightens the device.

In some applications of the present invention, the distal tissue coupling element and the proximal implant-penetrating element include respective elements that are coupled to one another.

In some applications of the present invention, the distal tissue coupling element and the proximal implant-penetrating element are fabricated from a single piece.

There is additionally provided, in accordance with some applications of the present invention apparatus, including:
 a tissue-repair implant configured to reside chronically in a heart of a patient;
 a tissue anchor including:
  a distal tissue coupling element configured to couple the tissue anchor to tissue of the heart of the patient; and
  a proximal implant-receiving element configured to receive at least a portion of the tissue-repair implant and facilitate coupling of the tissue-repair implant to the tissue anchor, the proximal implant-receiving element including:
 a proximal implant-restraining element coupled to a proximal portion of the implant-receiving element, the proximal implant-restraining element being configured to restrain the implant from separating from the implant-receiving element.

In some applications of the present invention, the proximal restraining element includes a protrusion configured to protrude into a plane of the implant and to couple the implant to the tissue anchor.

In some applications of the present invention, the protrusion is shaped so as to define a distal shelf that has a transverse cross-sectional length that is larger than a transverse cross-sectional length of the implant-receiving element, the distal shelf being configured to facilitate restricting of proximal motion of the implant along the protrusion.

In some applications of the present invention, the apparatus further includes a cord removably couplable to the tissue anchor, the cord being configured to facilitate passage of the implant therealong and toward the tissue anchor.

In some applications of the present invention, the cord passes through a portion of the implant-receiving element.

In some applications of the present invention, the proximal implant-receiving element includes a post.

In some applications of the present invention, the post has a length of between 1 and 7 mm and a greatest cross-sectional area of between 0.03 mm^2 and 0.2 mm^2, which length is at least 4 times the square root of the greatest cross-sectional area.

In some applications of the present invention, the length of the post is at least 5 times the square root of the greatest cross-sectional area of the post.

In some applications of the present invention, the length of the post is at least 8 times the square root of the greatest cross-sectional area of the post.

In some applications of the present invention, the length of the post is at least 10 times the square root of the greatest cross-sectional area of the post.

In some applications of the present invention, the length of the post is at least 15 times the square root of the greatest cross-sectional area of the post.

In some applications of the present invention, the proximal implant-restraining element is coupled to the post within 2 mm of a proximal end of the post.

In some applications of the present invention, the proximal implant-restraining element is shaped so as to define an opening therethrough, through which the cord is configured to pass.

In some applications of the present invention, the proximal implant-restraining element has a greatest cross-sectional area that is at least 1.5 times a greatest cross-sectional area of the post.

In some applications of the present invention, the apparatus further includes a lock configured to be advanced toward the anchor and disposed between the implant and the proximal implant-restraining element, the lock including:
 a distal portion configured to rest against the implant; and
 an expandable proximal portion having a cross-sectional area during a resting state of the lock that is larger than the greatest cross-sectional area of the post and smaller than the greatest cross-sectional area of the proximal implant-restraining element.

In some applications of the present invention, the proximal implant-restraining element includes a barb configured to restrict proximal movement of the implant along the implant-receiving element.

In some applications of the present invention, the barb includes one or more arms that are radially expandable to rest against an external surface of the implant following coupling of the implant to the implant-receiving element.

In some applications of the present invention, the arms are radially collapsible during at least a portion of the coupling of the implant to the implant-receiving element.

In some applications of the present invention, the proximal implant-receiving element includes an elastic portion that is configured to assume a first length when relaxed, and a second, greater length when under load.

In some applications of the present invention, the elastic portion includes a tension spring.

In some applications of the present invention, the proximal implant-receiving element has a length of between 3 and 5 mm when the elastic portion is relaxed.

In some applications of the present invention, the distal tissue coupling element is shaped so as to define a shape selected from the group consisting of: a helix, a spiral, and a screw shaft.

In some applications of the present invention, the distal tissue coupling element is shaped so as to define one or more radially-expandable prongs, the prongs being configured to expand and facilitate anchoring of the coupling element and restrict proximal motion of the tissue anchor.

In some applications of the present invention, the apparatus further includes the implant, the implant-receiving element is configured to couple the implant to the anchor.

In some applications of the present invention, the implant includes an annuloplasty device.

In some applications of the present invention, the implant includes:

a spool coupled to the tissue-repair implant; and a flexible contracting member that is coupled to the spool and the sleeve, such that winding the contracting member around the spool tightens the contracting member.

In some applications of the present invention, the distal tissue coupling element and the proximal implant-receiving element include respective elements that are coupled to one another.

In some applications of the present invention, the distal tissue coupling element and the proximal implant-receiving element are fabricated from a single piece.

There is also provided, in accordance with some applications of the present invention, the following inventive concepts:

1. A method comprising:

coupling, to cardiac tissue of a patient, a distal tissue coupling element of a tissue anchor, which tissue anchor further includes (a) a proximal implant-penetrating element, which is shaped so as to define a passage therethrough, which passage has at least two openings that are within 1 mm of a proximal end of the implant-penetrating element, and (b) a cord, which is removably passed through the passage;

passing the cord through an implant; and advancing the implant over the cord until the implant reaches and is penetrated by the proximal implant-penetrating element.

2. The method according to inventive concept 1, wherein coupling the distal tissue coupling element comprises:

coupling a distal tissue coupling element that comprises one or more radially-expandable prongs configured to expand and facilitate anchoring of the coupling element, and by the coupling, restricting proximal motion of the tissue anchor.

3. The method according to inventive concept 1, wherein the proximal implant-penetrating element includes a post, and wherein advancing comprises advancing the implant until the implant reaches and is penetrated by the post.

4. The method according to inventive concept 3, further comprising restraining the implant from separating from the implant-penetrating element by coupling a proximal restraining element to the post within 2 mm of the proximal end of the post.

5. The method according to inventive concept 4, wherein restraining the implant comprises advancing a lock along the cord to between the implant and the proximal restraining element, the lock including (a) a distal portion configured to rest against the implant, and (b) an expandable proximal portion having a cross-sectional area at its resting state that is larger than a greatest cross-sectional area of the post and smaller than a greatest cross-sectional area of the proximal restraining element.

6. The method according to inventive concept 1, wherein the proximal implant-penetrating element includes a barb, and wherein the method further comprises restraining the implant from separating from the implant-penetrating element by penetrating the barb through the implant.

7. The method according to inventive concept 6, wherein the barb includes one or more arms that are radially expandable, and wherein the method further comprises:

passing the one or more arms through the implant in a compressed state thereof, and restraining the implant from separating from the implant-penetrating element by allowing the one or more arms to expand and rest against an outer surface of the implant following the penetrating of the barb through the implant.

8. The method according to inventive concept 6, wherein the proximal implant-penetrating element includes an elastic portion that is configured to assume a first length when relaxed, and a second, greater length when under load, and wherein penetrating the barb through the implant comprises pulling the barb through the implant by pulling on the cord.

9. The method according to inventive concept 8, wherein the elastic portion includes a tension spring.

10. The method according to inventive concept 3, wherein the proximal restraining element is coupled within 2 mm of the proximal end of the post, and wherein restraining the implant from separating from the implant-penetrating element comprises restraining the implant from separating from the implant-penetrating element by the proximal restraining element is coupled within 2 mm of the proximal end of the post.

11. The method according to inventive concept 3, further comprising restraining the implant from separating from the implant-penetrating element by a proximal restraining element that is coupled to a proximal end of the post.

12. The method according to inventive concept 11, wherein restraining the implant comprises advancing a lock along the cord to between the implant and the proximal restraining element, the lock including (a) a distal portion configured to rest against the implant, and (b) an expandable proximal portion having a cross-sectional area at its resting state that is larger than a greatest cross-sectional area of the post and smaller than a greatest cross-sectional area of the proximal restraining element.

13. The method according to inventive concept 11, wherein the proximal implant-penetrating element includes a barb, and wherein restraining the implant from separating from the implant-penetrating element comprises penetrating the barb through the implant.

14. The method according to inventive concept 13, wherein the barb includes one or more arms that are radially expandable, and wherein the method further comprises:

passing the one or more arms through the implant in a compressed state thereof, and restraining the implant from separating from the implant-penetrating element by allowing the one or more arms to expand and rest against an outer surface of the implant following the penetrating of the barb through the implant.

15. The method according to inventive concept 13, wherein the proximal implant-penetrating element includes an elastic portion that is configured to assume a first length when relaxed, and a second, greater length when under load, and wherein penetrating the barb through the implant comprises pulling the barb through the implant by pulling on the cord.

16. The method according to inventive concept 15, wherein the elastic portion includes a tension spring.

17. The method according to inventive concept 1, wherein coupling comprises coupling the distal tissue coupling element to the tissue at a site within a heart chamber of the patient, and wherein the method further comprises, after the advancing of the implant over the cord:

cutting the cord at a site outside of the heart chamber; and
withdrawing the cord from the passage.

18. The method according to inventive concept 1, wherein coupling comprises coupling the distal tissue coupling element to the tissue at a site within a heart chamber of the patient, and wherein the method further comprises, after the advancing of the implant over the cord, withdrawing the cord from the passage.

19. The method according to inventive concept 1, wherein the implant includes an annuloplasty device, and wherein advancing the implant comprises advancing the device over the cord until the device reaches and is penetrated by the proximal implant-penetrating element.

20. The method according to inventive concept 19, wherein coupling the distal tissue coupling element and advancing the device comprise coupling and advancing during a transcatheter procedure.

21. The method according to inventive concept 19, wherein advancing the device comprises advancing the device into an atrium of a heart of the patient in a vicinity of an annulus of an atrioventricular valve.

22. The method according to inventive concept 19, further comprising tightening the annuloplasty device by winding a flexible contracting member of the device around a spool coupled to the device.

23. A method comprising:

coupling, to a first portion of cardiac tissue of a patient, a distal tissue coupling element of a tissue anchor, which tissue anchor further includes (a) a proximal implant-receiving element, and (b) a cord, which is removably coupled to the implant-receiving element;

passing the cord through a tissue-repair implant;

advancing the implant over the cord until the implant reaches and is received at least in part by the proximal implant-receiving element, the proximal implant-receiving element comprising a proximal implant-restraining element; and restraining the implant from separating from the implant-receiving element by the proximal implant-restraining element.

24. The method according to inventive concept 23, wherein coupling the distal tissue coupling element comprises:

coupling a distal tissue coupling element that comprises one or more radially-expandable prongs configured to expand and facilitate anchoring of the coupling element, and by the coupling, restricting proximal motion of the tissue anchor.

25. The method according to inventive concept 23, wherein the proximal implant-receiving element includes a post, wherein the proximal implant-restraining element is coupled to a proximal portion of the post, and wherein advancing comprises advancing the implant until the implant reaches and is penetrated by the post.

26. The method according to inventive concept 25, wherein the proximal restraining element is coupled within 2 mm of the proximal end of the post, and wherein restraining the implant from separating from the implant-penetrating element comprises restraining the implant from separating from the implant-penetrating element by the proximal restraining element is coupled within 2 mm of the proximal end of the post.

27. The method according to inventive concept 25, wherein restraining the implant comprises advancing a lock along the cord to between the implant and the proximal restraining element, the lock including (a) a distal portion configured to rest against the implant, and (b) an expandable proximal portion having a cross-sectional area at its resting state that is larger than a greatest cross-sectional area of the post and smaller than a greatest cross-sectional area of the proximal implant-restraining element.

28. The method according to inventive concept 23, wherein the proximal implant-restraining element includes a barb, and wherein the method further comprises restraining the implant from separating from the implant-receiving element by penetrating the barb through at least a portion of the implant.

29. The method according to inventive concept 28, wherein the barb includes one or more arms that are radially expandable, and wherein the method further comprises:

passing the one or more arms through the implant in a compressed state thereof, and restraining the implant from separating from the implant-receiving element by allowing the one or more arms to expand and rest against an outer surface of the implant following the penetrating of the barb through the implant.

30. The method according to inventive concept 28, wherein the proximal implant-receiving element includes an elastic portion that is configured to assume a first length when relaxed, and a second, greater length when under load, and wherein penetrating the barb through the implant comprises pulling the barb through the implant by pulling on the cord.

31. The method according to inventive concept 30, wherein the elastic portion includes a tension spring.

32. The method according to inventive concept 23, wherein coupling comprises coupling the distal tissue coupling element to the tissue at a site within a heart chamber of the patient, and wherein the method further comprises, after the advancing of the implant over the cord:

cutting the cord at a site outside of the heart chamber; and
withdrawing the cord from the passage.

33. The method according to inventive concept 23, wherein coupling comprises coupling the distal tissue coupling element to the tissue at a site within a heart chamber of the patient, and wherein the method further comprises, after the advancing of the implant over the cord, withdrawing the cord from the tissue anchor.

34. The method according to inventive concept 23, wherein coupling the distal tissue coupling element and advancing the implant comprise coupling and advancing during a transcatheter procedure.

35. The method according to inventive concept 23, wherein advancing the implant comprises advancing the device into an atrium of a heart of the patient in a vicinity of an annulus of an atrioventricular valve.

36. The method according to inventive concept 23, further comprising adjusting a distance between the first portion of cardiac tissue and a second portion of cardiac tissue by winding a flexible contracting member of the device around a spool coupled to the implant.

37. The method according to inventive concept 23, wherein the implant includes an annuloplasty device, and wherein advancing the implant comprises advancing the device over the cord until the device reaches and is penetrated by the proximal implant-receiving element.

38. The method according to inventive concept 37, further comprising tightening the annuloplasty device by winding a flexible contracting member of the device around a spool coupled to the device.

The present invention will be more fully understood from the following detailed description of applications thereof, taken together with the drawings, in which:

BRIEF DESCRIPTION OF THE DRAWINGS

FIGS. 2A-C are schematic illustrations of the tissue anchor and a delivery tool therefor, in accordance with some applications of the present invention;

FIGS. 5A-B, 6A-B, and 7 are schematic illustrations of respective locking mechanisms for each of the tissue anchors of FIGS. 3-4, in accordance with some applications of the present invention;

FIGS. 8 and 9 are schematic illustrations of examples of valve-repair implants which are received by the tissue anchors of FIGS. 3-4, in accordance with respective applications of the present invention;

FIGS. 11A-D are schematic illustrations of a transcatheter procedure for implanting a plurality of tissue anchors of FIG. 10, in accordance with some applications of the present invention;

FIGS. 12-14 are schematic illustrations of a manipulator for implanting the tissue anchors or FIGS. 2A-C and 10 during a minimally-invasive or open-heart procedure, in accordance with some applications of the present invention;

FIG. 19 is a schematic illustration of the tissue anchor of FIGS. 2A-C in accordance with some applications of the present invention; and FIG. 20 is a schematic illustration of the tissue anchor of FIG. 10, in accordance with some applications of the present invention.

DETAILED DESCRIPTION OF APPLICATIONS

Figure 1A:
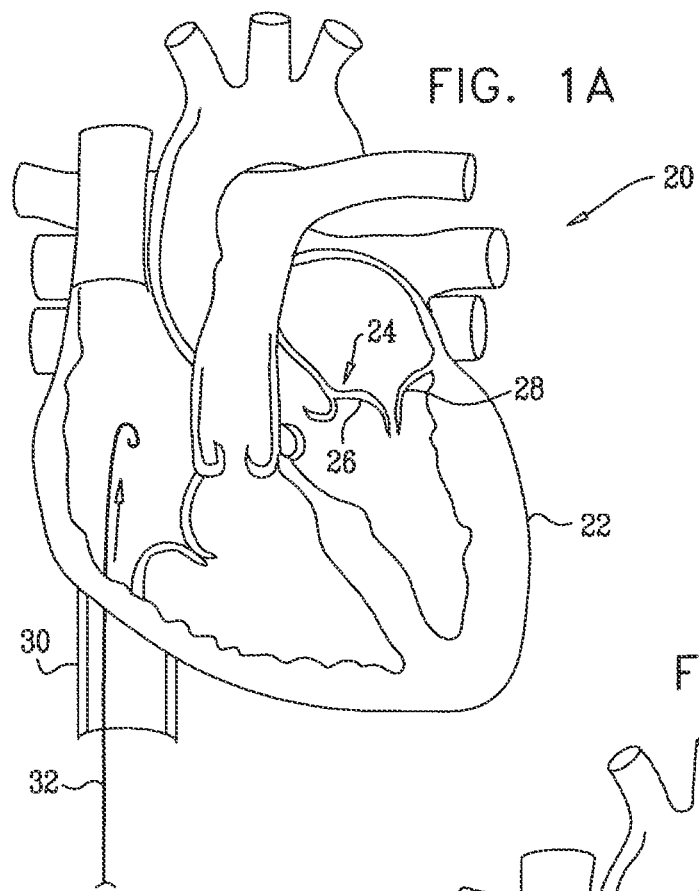
FIGS. 1A-F are schematic illustrations of a procedure for implanting a tissue anchor for receiving a valve-repair implant, in accordance with some applications of the present invention.

Reference is now made to FIGS. 1A-F, 2A-C, and 3, which are schematic illustrations of a system 20 for implanting a tissue anchor 49, in accordance with some applications of the present invention. FIGS. 1A-F show a transcatheter procedure for implanting tissue anchor 49. FIGS. 2A-C show a transcatheter delivery tool 42 for delivering toward and implanting anchor 49 at an implantation site, e.g., an annulus 25 of a heart 22 of a patient, as shown. Typically, the implantation site includes an annulus of an atrioventricular valve, e.g., a mitral valve or a tricuspid valve. It is to be noted that the implantation site is not limited to a heart valve of the patient, and anchor 49 may be implanted in other tissue of the patient, e.g., a portion of the inner wall of the heart of the patient, in a stomach of a patient, etc. Tissue anchor 49, as shown in FIG. 2B comprises a distal tissue coupling element 50, e.g., a helical tissue anchor 58, and a proximal implant-penetrating element 47a. Proximal implant-penetrating element 47a comprises a post 52a and a proximal implant-restraining element 53a which is configured to puncture and pass through a portion of a valve-repair implant, as will be described hereinbelow. Proximal restraining element 53a (i.e., a portion of implant-penetrating element 47a) is shaped so as to define a passage 56 therethrough. A cord 54 is removably coupled to anchor 49 by being passed through passage 56. Cord 54 functions to facilitate guiding of the valve-repair implant toward tissue anchor 49 implanted at annulus 25.

Reference is now made to FIGS. 1A-F, 2A-C, and 3-4 which are schematic illustrations of a procedure for implanting a plurality of tissue anchors 49 in order to repair a mitral valve 24 of the patient, in accordance with some applications of the present invention. Mitral valve 24 is shown including leaflets 26 and 28. The procedure is typically performed with the aid of imaging, such as fluoroscopy, transesophageal echo, and/or echocardiography.

The procedure typically begins by advancing a semi-rigid guidewire 32 into a right atrium of the patient, as shown in FIG. 1A.

Figure 1B:
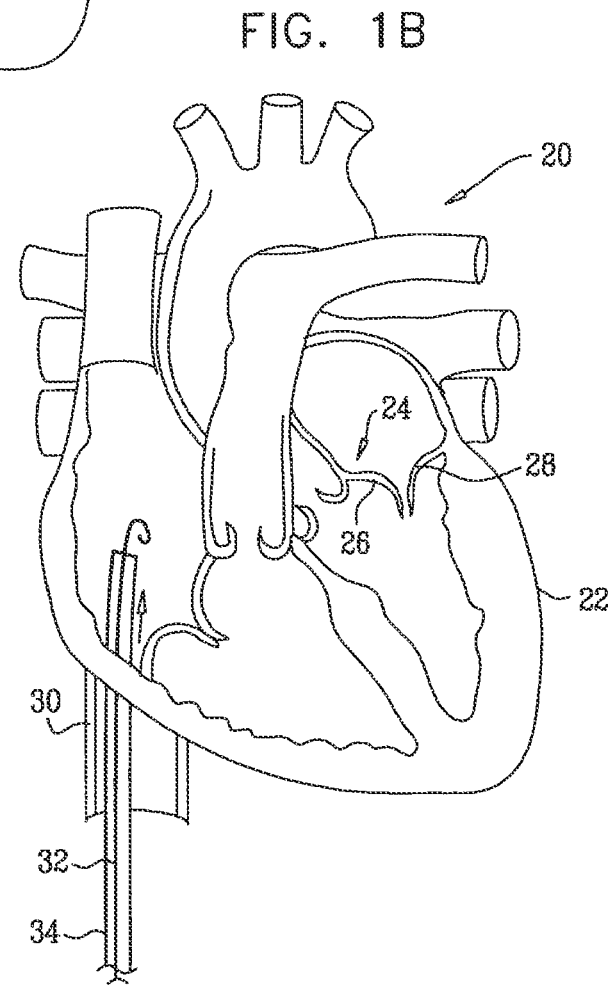

As show in FIG. 1B, guidewire 32 provides a guide for the subsequent advancement of a sheath 34 therealong and into the right atrium. Once sheath 34 has entered the right atrium, guidewire 32 is retracted from the patient's body. Sheath 34 typically comprises a 14-20 F sheath, although the size may be selected as appropriate for a given patient. Sheath 34 is advanced through vasculature into the right atrium using a suitable point of origin typically determined for a given patient. For example:

sheath 34 may be introduced into the femoral vein of the patient, through an inferior vena cava 30, into the right atrium, and into a left atrium transseptally, typically through the fossa ovalis;

sheath 34 may be introduced into the basilic vein, through the subclavian vein to the superior vena cava, into the right atrium, and into the left atrium transseptally, typically through the fossa ovalis; or sheath 34 may be introduced into the external jugular vein, through the subclavian vein to the superior vena cava, into the right atrium, and into the left atrium transseptally, typically through the fossa ovalis.

In some applications of the present invention, sheath 34 is advanced through an inferior vena cava 30 of the patient (as shown) and into the right atrium using a suitable point of origin typically determined for a given patient.

(In this context, in the specification and in the claims, "proximal" means closer to the orifice through which system 20 is originally placed into the body of the patient, and "distal" means further from this orifice.)

Figure 1C:
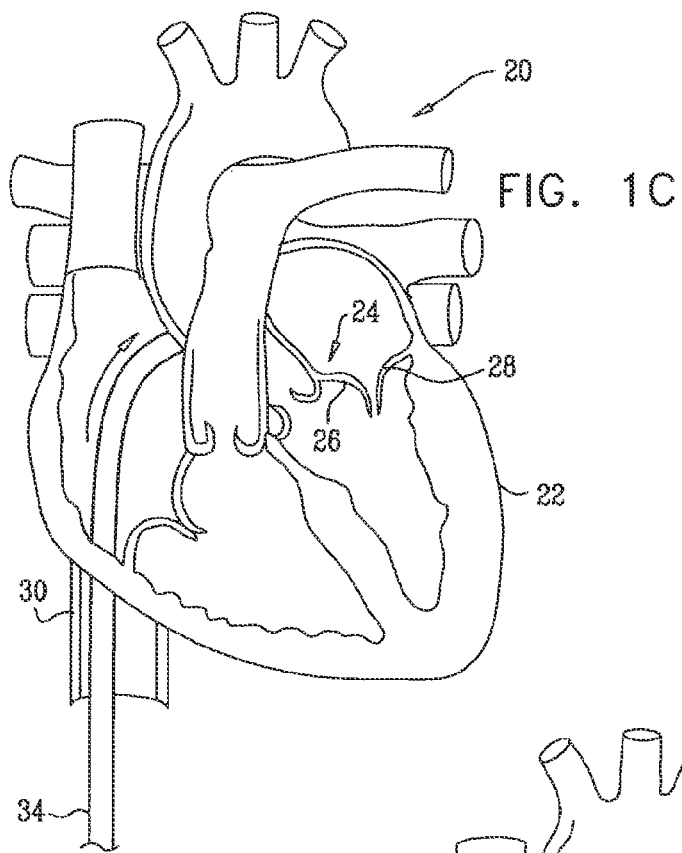

Sheath 34 is advanced distally until the sheath reaches the interatrial septum, as shown in FIG. 1C.

Figure 1D:
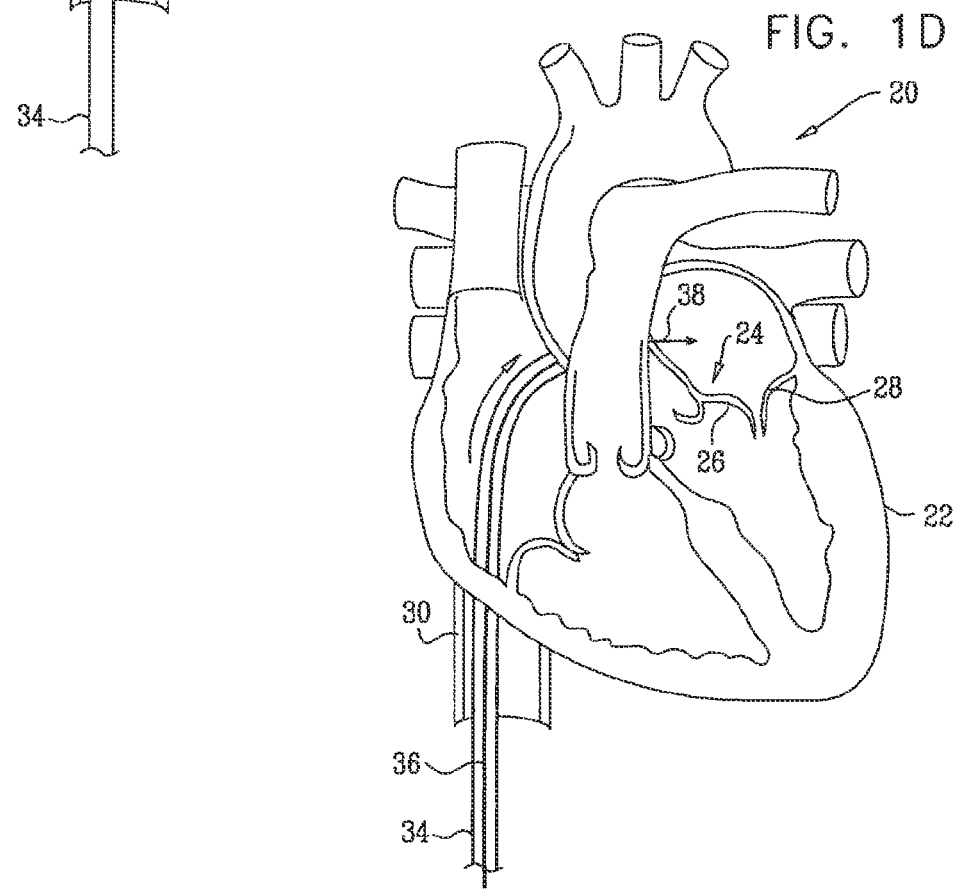

As shown in FIG. 1D, a resilient needle 38 coupled to en elongate wire 36 and a dilator (not shown) are advanced through sheath 34 and into heart 22. In order to advance sheath 34 transseptally into the left atrium, the dilator is advanced to the septum, and needle 38 is pushed from within the dilator and is allowed to puncture the septum to create an opening that facilitates passage of the dilator and subsequently sheath 34 therethrough and into the left atrium. The dilator is passed through the hole in the septum created by the needle. Typically, the dilator is shaped to define a hollow tube shaft for passage along needle 38, and the hollow tube shaft is shaped to define a tapered distal end. This tapered distal end is first advanced through the hole created by needle 38. The hole is enlarged when the gradually increasing diameter of the distal end of the dilator is pushed through the hole in the septum.

Figure 1E:
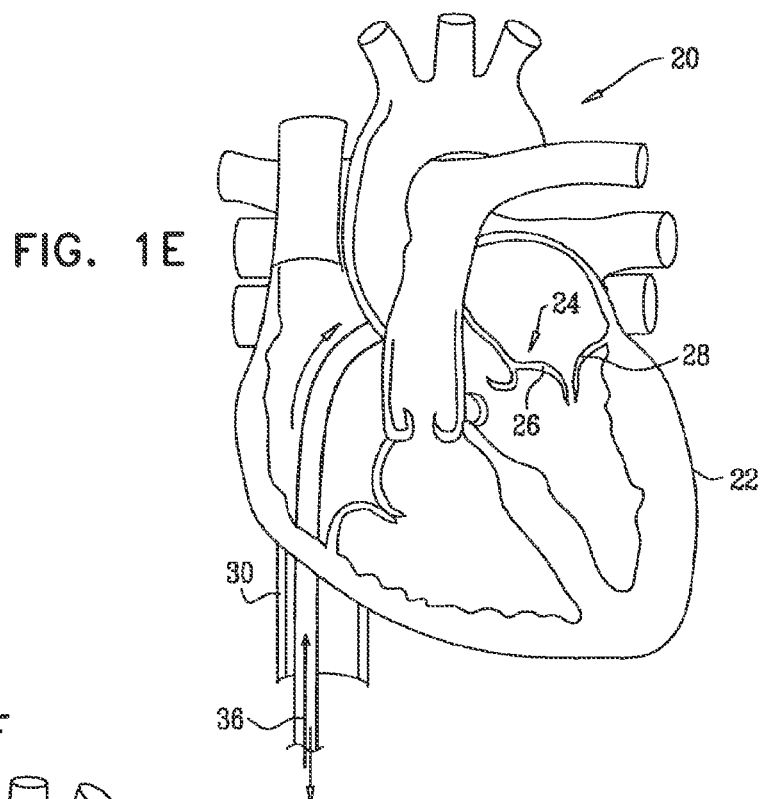

The advancement of sheath 34 through the septum and into the left atrium is followed by the extraction of the dilator and needle 38 from within sheath 34, as shown in FIG. 1E.

Figure 1F:
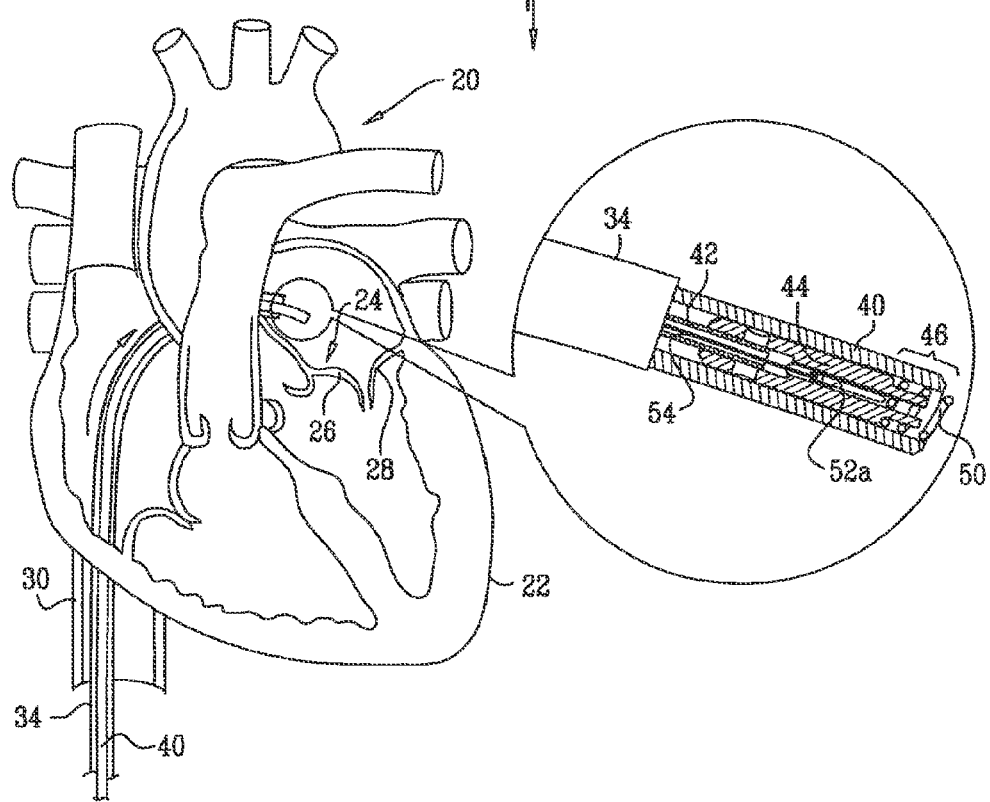

Subsequently, as shown in FIG. 1F, delivery tool 42 is advanced within an advancement catheter 40 and through sheath 34. Delivery tool 42 comprises an elongate tube shaft that is coupled at a distal end thereof to a manipulator 44. Manipulator 44 reversibly engages anchor 49 and facilitates the delivery of anchor 49 to the left atrium and the subsequent implantation of anchor 49 in tissue of annulus 25 of the patient. Delivery tool 42 is described hereinbelow with reference to FIGS. 2A-C.

FIG. 2A shows delivery tool 42 disposed within advancement catheter 40, which slides through sheath 34 and toward annulus 25 of heart 22. Delivery tool 42, manipulator 44, and anchor 49 are shown in cross-section.

FIG. 2B shows the relative spatial configurations of delivery tool 42, manipulator 44, and anchor 49. Anchor 49 comprises a distal tissue coupling element 50 having a pointed distal tip 51 configured for puncturing tissue of the patient. Distal tissue coupling element 50 comprises a helical tissue anchor 58, by way of illustration and not limitation, e.g., tissue coupling element 50 may comprise any suitable tissue anchor known in the art (e.g., as is shown hereinbelow in FIGS. 19 and 20). For example, distal tissue coupling element 50 may comprise any suitable tissue anchor known in the art (e.g., a spiral or a screw shaft) or any tissue anchor as described in PCT Patent Application PCT/IL2009/000593 to Gross et al., entitled, "Annuloplasty devices and methods of delivery therefor," filed Jun. 15, 2009, which published as WO 10/004546, and which is incorporated herein by reference.

Reference is now made to FIGS. 2A-B. The helical coils of helical tissue anchor 58 form a generally-cylindrical coil surrounding a lumen of helical tissue anchor 58. Helical tissue anchor 58 is shaped to provide a bar 55 which projects into the lumen of helical tissue anchor 58. A distal portion 57 of implant-penetrating element 47a is coupled, e.g., welded, to bar 55.

Reference is again made to FIG. 2B. Anchor 49, comprising distal tissue coupling element 50 and implant-penetrating element 47a, has a length L1 of 6-18, e.g., 6-12 mm, e.g., 10 mm. In some applications of the present invention, distal tissue coupling element 50 and implant-penetrating element 47a are separate pieces that are coupled, e.g., welded, to one another. Alternatively, distal tissue coupling element 50 and implant-penetrating element 47a are fabricated from a single piece. Implant-penetrating element 47a has a length L2 of 4-10 mm, e.g., 5.5 mm. Distal tissue coupling element 50 has a length L3 of 2-8 mm, e.g., 4 mm. Implant-penetrating element 47a comprises a post 52a and proximal restraining element 53a. Post 52a has a length of between 1 and 7 mm, e.g., 5.5 mm and a greatest cross-sectional area (measured at a plane that is perpendicular to the axis along which the length of post 52a is measured) of between 0.03 and 0.2 mm^2, e.g., 0.13 mm^2, which length is at least 4 times (e.g., 5, 8, or 10 times) the square root of the greatest cross-sectional area. Post 52a has a longest dimension at its cross-section of between 0.2 mm and 0.5 mm (e.g., 0.4 mm). That is, for example, post 52a has a length of 5.5 mm and a longest cross-sectional dimension (measured at the plane that is perpendicular to the axis along with the length of post 52a is measured) of 0.4 mm. In such an example, the ratio of the length to the longest cross-sectional dimension is around 13.75:1. For some applications, this ratio is between 5:1 and 14:1, and the ratio varies depending on the size of the implant that is anchored to the tissue of the patient via anchor 49.

It is to be noted that anchors 49 may be used to implant any implant of any suitable size to any tissue of the patient, and that the ratio of length to the longest cross-sectional dimension of post 52a of between 5:1 and 14:1 varies depending on the size of the implant that is anchored to the patient.

Proximal restraining element 53a, is coupleable or coupled to post 52a within 2 mm of the proximal end of post 52a. For some applications, as recited above, implant-penetrating element 47a comprises proximal restraining element 53a. Proximal restraining element 53a has a longest dimension at its cross-section (measured at a plane that is perpendicular to the axis along which the length L1 is measured) of between 0.3 mm and 0.75 mm, e.g., 0.6 mm. Proximal restraining element 53a has a greatest cross-sectional area of between 0.07 and 0.44 mm^2, (e.g., 0.28 mm^2) that is at least 1.5 times a greatest cross-sectional area of post 52a. Following the subsequent implantation of the valve-repair implant, as will be described hereinbelow, proximal restraining element 53a restrains the implant from sliding proximally along post 52a and separating from implant-penetrating element 47a. Implant-penetrating element 47a is thus shaped to provide an elongate penetration having a sufficient length-to-width ratio for penetrating the implant and for passing through the lumen of the implant such that proximal restraining element 53a is disposed proximally to the outer surface of the implant. In this configuration, proximal restraining element 53a restrains the implant from separating from implant-penetrating element 47a, as is described hereinbelow.

Proximal restraining element 53a is shaped so as to define a passage 56 therethrough, which passage has at least two openings that are within 1 mm, e.g., such as 0.5 mm, of a proximal end of implant-penetrating element 47a. Cord 54 is looped through passage 56 and is thereby removably coupled to anchor 49. As shown in FIG. 2C, the two portions of cord 54 that project away from passage 56 of proximal restraining element 53a, are joined, e.g., welded, together at site proximal to tissue anchor 49, e.g., at a site outside the body of the patient, in order to form a single proximal end portion 59 of cord 54. End portion 59 of cord 54 is ultimately threaded through the implant outside the body of the patient in order for the implant to be slid along cord 54 and toward tissue anchor 49 at annulus 25. Once the implant is implanted at the annulus of the patient, cord 54 is cut distally to single proximal end portion 59 so as to sever the loop created by the joining of the two portions of cord 54 at end portion 59. Once cord 54 is cut, the physician extracts cord 54 from within the body of the patient as he or she pulls on proximal end portion 59 until cord 54 is pulled from within passage 56 of proximal restraining element 53a and is decoupled from anchor 49.

Reference is again made to FIG. 2A. As shown in the cross-sectional illustration, delivery tool 42 and manipulator 44 are each shaped so as to define a central lumen for cord 54 that is coupled to proximal restraining element 53a of implant-penetrating element 47a. Cord 54 comprises a wire, a ribbon, a rope, or a band, which typically comprises a flexible and/or superelastic material, e.g., nitinol, ePTFE, PTFE, polyester, stainless steel, or cobalt chrome. In some applications of the present invention, cord 54 comprises a braided polyester suture (e.g., Ticron). In some applications of the present invention, cord 54 is coated with polytetrafluoroethylene (PTFE). In some applications of the present invention, cord 54 comprises a plurality of wires that are intertwined to form a rope structure.

Manipulator 44 is disposed at the distal end of the tube shaft of delivery tool 42 and is shaped to provide a distal applicator portion 46 which has a smaller outer diameter than an outer diameter of a proximal portion of manipulator 44. As shown in the cross-sectional illustration of manipulator 44 and anchor 49 in FIG. 2A, distal applicator portion 46 is shaped so as to fit within a lumen of distal tissue coupling element 50 (i.e., the outer diameter of portion 46 is smaller than an inner diameter of distal tissue coupling element 50). Manipulator 44 is shaped so as to define a slit 48 which bisects the distal end portion of manipulator 44 into two lateral walled portions. Slit 48 functions as a housing for housing and reversibly coupling implant-penetrating element 47a to delivery tool 42 (as shown in FIG. 2A). Slit 48 holds in place anchor 49 as it is advanced toward annulus 25. Delivery tool 42 then functions to implant distal tissue coupling element 50 of anchor 49 in tissue of annulus 25. First, torque is delivered toward manipulator 44 in response to rotation of the tube shaft of delivery tool 42. Responsively to the torque, the lateral walled portions at the distal portion of manipulator 44 and distal applicator portion 46 function as a screw-driving tool by applying annular force to implant-penetrating element 47a and helical tissue anchor 58.

As shown in FIG. 2A, bar 55 of distal tissue coupling element 50 functions to couple anchor 49 to manipulator 44 when bar 55 is received and disposed within slit 48 and surrounded by the lateral wall portions of manipulator 44.

Figure 3:
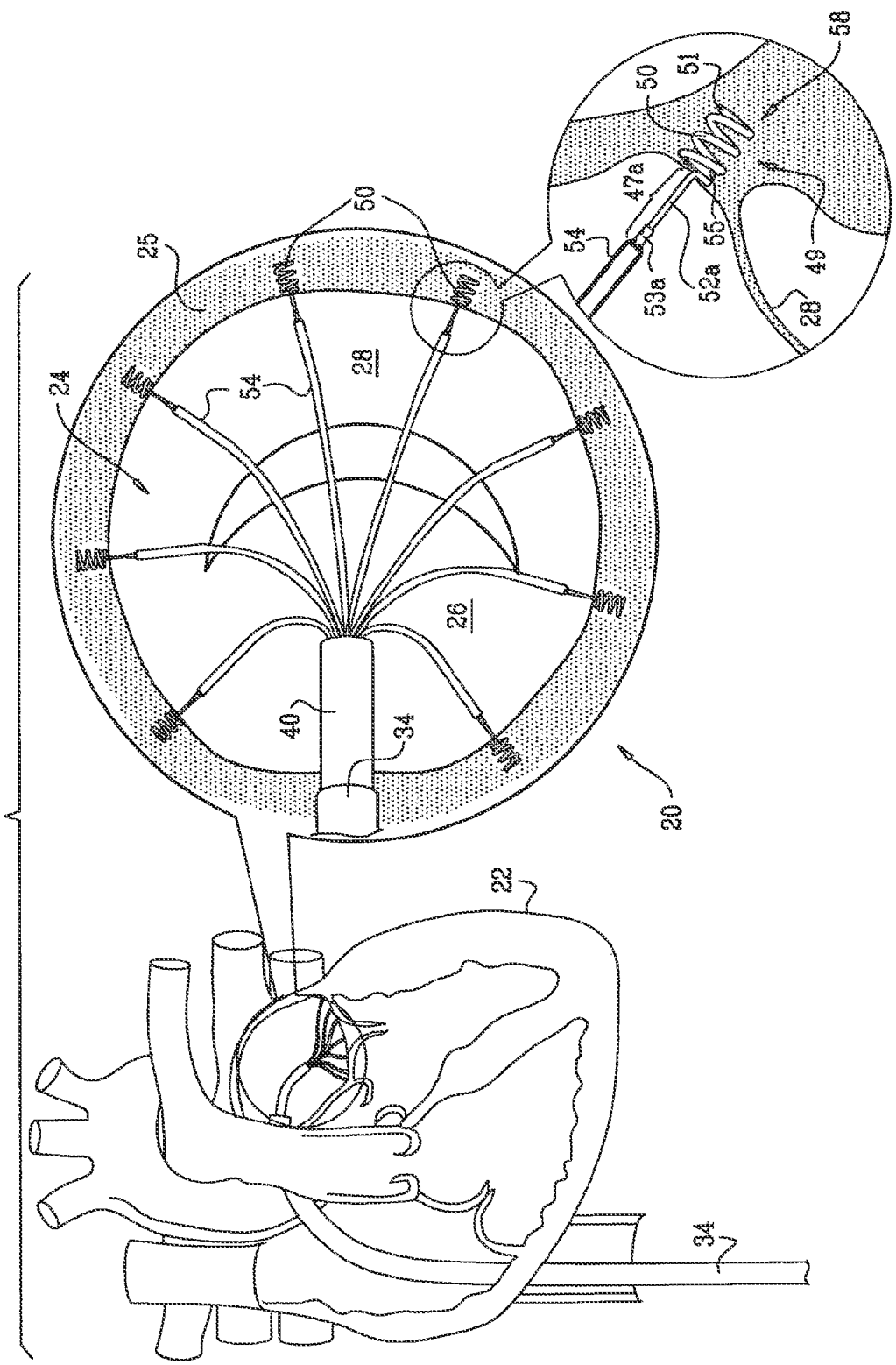
FIG. 3 is a schematic illustration of a plurality of the tissue anchors of FIGS. 2A-C implanted along an annulus of a patient, in accordance with some applications of the present invention.

FIG. 3 shows a plurality of anchors 49 implanted in respective portions of tissue of annulus 25 around a perimeter thereof. Each anchor 49 is implanted such that a central longitudinal axis therethrough forms an angle of between about 45 and 90 degrees with a surface of the tissue of annulus 25, such as between about 75 and 90 degrees, e.g., about 90 degrees. The physician uses delivery tool 42, as described hereinabove to systematically advance each anchor 49 through sheath 34 and toward annulus 25. A first anchor 49 is coupled to manipulator 44 of delivery tool 42, as follows: (a) cord 45 is fed through the lumen of the tube shaft of delivery tool 42 and through the lumen of manipulator 44, and (b) distal applicator portion 46 of manipulator 44 is advanced within the lumen of helical tissue anchor 58, while (c) bar 55 of helical tissue anchor 58 is advanced in place within slit 48 of manipulator 44. The relative spatial configurations anchor 49 and manipulator 44 when anchor 49 is coupled to manipulator 44 is shown hereinabove with reference to FIG. 2A.

Delivery tool 42 is then fed within advancement catheter 40, and catheter 40 is advanced within sheath 34 toward annulus 25 until a distal end of catheter 40 emerges from within the distal end of sheath 34 and into the left atrium of the patient. Advancement catheter 40 is advanced toward a given location along annulus 25. Subsequently, the tube shaft of delivery tool 42 is pushed such that distal tip 51 of helical tissue anchor 58 abuts the surface of tissue of the annulus. Torque is then delivered to manipulator 44 when the physician rotates the tube shaft of delivery tool 42 about a central axis of tool 42. Such rotation of tool 42 rotates manipulator 44 in a manner in which the distal walled portions of the distal end of manipulator 44 apply an annular force to helical tissue anchor 58. Responsively to the continued application of the annular force to helical tissue anchor 58, distal tip 51 punctures the tissue of annulus 25 and continues along a helical path until helical tissue anchor 58 is corkscrewed sufficiently into tissue of annulus 25 at the given location. For applications in which distal tissue coupling element 50 comprises any other tissue coupling anchor, delivery tool 42 or any other delivery tool facilitates coupling of anchor 49 to annulus 25 by advancing distal tissue coupling element 50 into the tissue of annulus 25.

Following the corkscrewing of helical tissue anchor 58 into tissue of the annulus, the physician pulls slightly on the tube shaft of delivery tool 42. Upon applying the pulling force to tool 42, the tissue of the annulus responsively pulls on the corkscrewed distal tissue coupling element 50, thereby pulling implant-penetrating element 47a from within slit 48 of manipulator 44 and disengaging anchor 49 from tool 42. As implant-penetrating element 47a is pulled from and slides distally within slit 48, it frees anchor 49 from manipulator 44. Delivery tool 42, freed from anchor 49, is then retracted within catheter 40, and catheter 40 is extracted from within the body through sheath 34 which remains in place for the subsequent advancements of the remaining anchors 49. As delivery tool 42 and catheter 40 are extracted, cord 45 remains looped within passage 56 of proximal restraining element 53a and is left disposed within sheath 34 such that proximal end portion 59 of cord 54 is disposed and accessible outside the body of the patient.

Once outside the body of the patient, delivery tool 42 is then coupled to a second anchor 49 (as described hereinabove with reference to the coupling of anchor 49 to manipulator 44), and tool 42 is fed into advancement catheter 40 which is then reintroduced into sheath 34. The second anchor 49 is implanted, as described hereinabove. These steps are repeated until all of the anchors have been implanted around annulus 25, as shown in FIG. 3. As shown, cords 45 reversibly coupled to each anchor 49 are disposed within sheath 34 and are accessible at their respective proximal portions 59 at a site outside the body of the patient. It is to be noted that although eight anchors 49 are implanted around annulus 25 by way of illustration and not limitation, any suitable number of anchors 49 may be implanted along annulus 25 according to the needs of a given patient, e.g., depending on the level of distention and relaxation of the annulus of a given patient.

Figure 4:
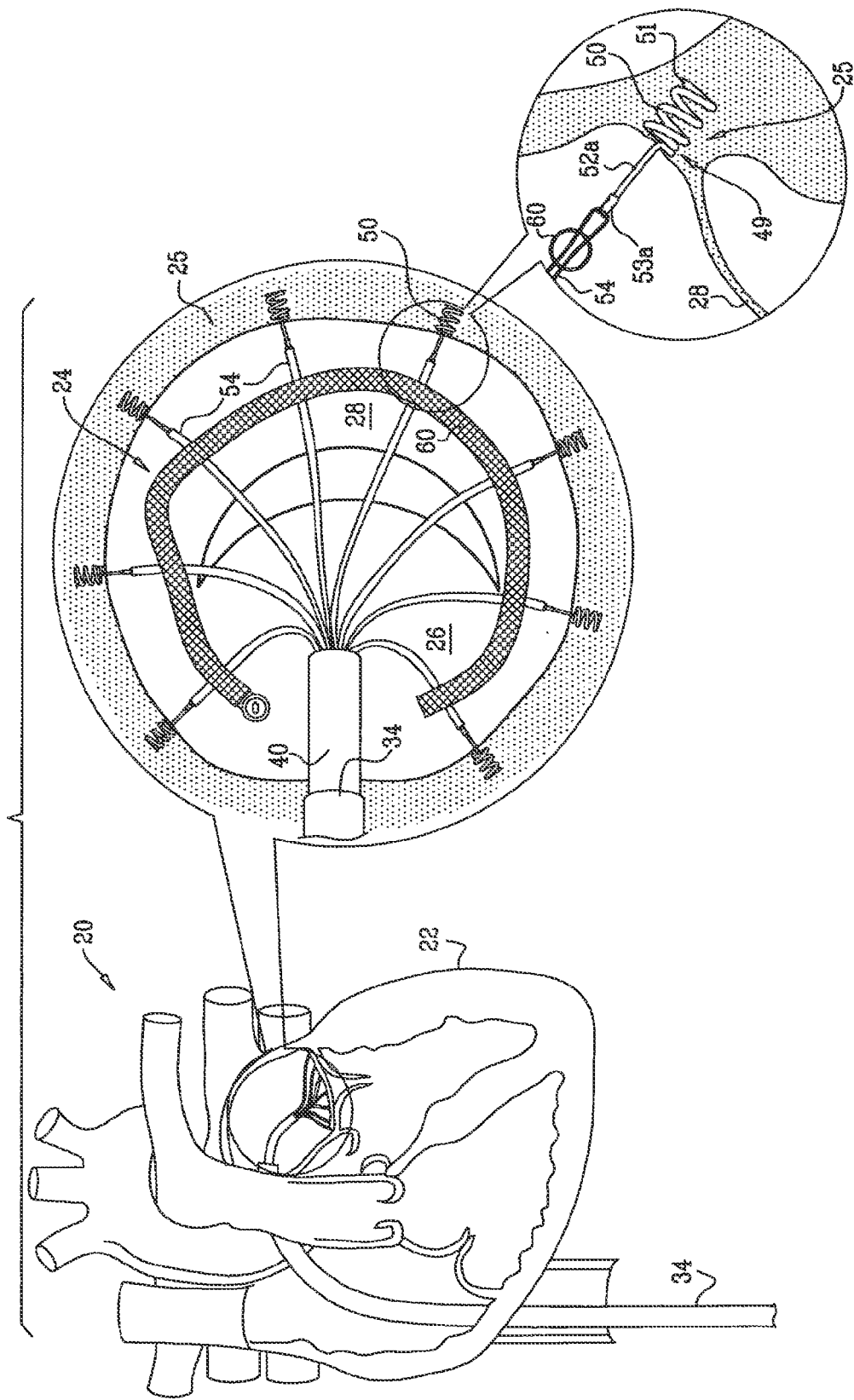
FIG. 4 is a schematic illustration of a valve-repair implant being advanced toward the plurality of anchors of FIG. 3, in accordance with some applications of the present invention.

Reference is now made to FIG. 4, which is a schematic illustration of a tissue-repair implant 60 being advanced along cords 54 toward annulus 25 of the mitral valve of the patient. As shown, repair implant 60 comprises a non-continuous, open, partial annuloplasty ring, by way of illustration and not limitation. It is to be noted that any valve-repair device, or implant (e.g., a full annuloplasty ring, a partial annuloplasty ring, a prosthetic valve, or a docking station for a prosthetic valve such as an annular valve support member) may be advanceable along cords 54. The partial, open ring of repair implant 60 may be implemented using any one of the techniques described in U.S. patent application Ser. No. 12/341, 960 to Cabiri, which published as 2010/0161047, which issued as U.S. Pat. No. 8,241,351, and which is incorporated herein by reference. Typically, these techniques describe a full or partial ring comprising a sleeve, a spool coupled to the sleeve, and a flexible contracting member that is coupled to the spool and the sleeve, such that (1) winding the contracting member around the spool tightens the ring, and (2) unwinding the contracting member from around the spool relaxes and expands the ring. As shown, implant 60 comprises a penetrable sleeve comprising a braided fabric mesh. Implant 60 may also comprise a coiled implant in addition to or independently of the sleeve.

Reference is made to FIGS. 2C and 4. Prior to the advancing of implant 60, a respective proximal end portion 59 of each cord 54 is threaded through the material of repair implant 60. For example, end portion 59 is threaded (a) through a first surface of implant 60, (b) through the lumen of implant 60 such that portion 59 passes orthogonal to the longitudinal axis defined by the lumen of implant 60, and then (c) through an opposing surface of implant 60 such that it emerges proximal to the outer surface of implant 60. A pushing tool (not shown for clarity of illustration) is used to advance implant 60 through advancement catheter 40 (which is advanced through sheath 34) and along each cord 54 toward annulus 25. Once implant 60 emerges from within catheter 40, the pushing tool is retracted and extracted from the body. Subsequently, implant 60 is locked in place along annulus 25 via anchors 49, as is described hereinbelow.

FIGS. 5A-B show a locking mechanism 74 that comprises a lock 80 having an annular distal portion 82 that is coupled to a plurality of radially-collapsible prongs 84, in accordance with some applications of the present invention. Annular distal portion 82 has a diameter of between 1.5 mm and 3 mm, e.g., 2.2 mm. Following the advancement of mechanism 74 through the vasculature of the patient, lock 80 is ultimately positioned at a proximal portion of post 52a of implant-penetrating element 47a at a site distal to implant-restraining element 53a (FIG. 5B), as described hereinbelow.

It is to be noted that lock 80 also functions as a proximal restraining element to restrain implant 60 from sliding proximally away from anchor 49 and annulus 25.

Locking mechanism 74 is coupled to a distal end of an advancement tube 72 and is advanced toward annulus 25 of the patient while surrounded by an overtube 70. Locking mechanism 74 comprises a lock holder 73 which has radially-expandable arms 75 and 77. Each of arms 75 and 77 is shaped to define a respective slot 81 and 83 which each cup and receive respective portions of annular distal portion 82 of lock 80, as shown in the enlarged image of FIG. 5A. A distal portion of overtube 70 surrounds arms 75 and 77 during the advancement of locking mechanism 74 toward annulus 25 of the patient. Overtube 70 thus prevents arms 75 and 77 from radially expanding, and this maintains coupling between holder 73 and lock 80. As shown, locking mechanism 74, advancement tube 72, and overtube 70 are advanced toward implant 60, along cord 54.

The distal ends of advancement tube 72 and overtube 70 are advanced until they contact a proximal surface of a portion of implant 60. In response to continued pushing of tubes 70 and 72, tubes 70 and 72 push the portion of implant 60 distally such that implant 60 is penetrated by implant-penetrating element 47a (i.e., first by proximal restraining element 53a and then by post 52a). For some applications, proximal restraining element 53a is shaped to define a pointed tip, e.g., a barb, configure to puncture and penetrate a portion of implant 60. Once implant 60 is fully pushed, a distal surface of implant 60 contacts tissue of annulus 25 and the proximal surface of implant 60 is disposed distally to a distal end of proximal restraining element 53a. Post 52a couples implant 60 to anchor 49 by extending through a lumen of implant 60.

It is to be noted that implant-penetrating element 47a may penetrate the implant by penetrating a braided mesh surrounding the implant, may penetrate the implant by passing between coils of a coiled implant, and/or may penetrate the implant in any other penetrating manner.

FIG. 5B shows the disengaging of lock 80 from mechanism 74 following the locking in place of implant 60 to anchor 49 via lock 80. As described hereinbelow, once lock 80 is coupled to anchor 49, overtube 70 is slid proximally with respect to advancement tube 72 such that arms 75 and 77 of lock holder 73 are exposed from within the distal portion of overtube 70. Once arms 75 and 77 are exposed, they expand radially (as is their natural tendency), and respective portions of annular distal portion 82 of lock 80 are freed from within slots 81 and 83 of arms 75 and 77, respectively. Once lock 80 is freed from locking mechanism 74, advancement tube 72, locking mechanism 74, and overtube 70 are retracted from within the body of the patient. In conjunction with the retracting, cord 54 is clipped and pulled such that it is no longer looped within passage 56 of proximal restraining element 53a. The physician continues to pull cord 54 until cord 54 is extracted from within the body of the patient.

FIGS. 6A-B and 7 show the method for locking repair implant 60 to annulus 25 via anchor 49, in accordance with some applications of the present invention. As shown, post 52a of anchor 49 extends through the lumen of implant 60 from a distal surface of implant 60 (i.e., the surface in contact with annulus 25) to an opposing surface at the proximal surface of implant 60 (i.e., the surface in communication with the atrium of the patient). Post 52a extends through the lumen of implant 60 in a manner in which a distal end of proximal restraining element 53a is disposed proximally to the proximal surface of implant 60.

Overtube 70 (and advancement tube 72, locking mechanism 74, and lock 80 disposed in overtube 70) is advanced along cord 54 and toward anchor 49 implanted at a given location along annulus 25. The distal end of overtube 70 approaches the proximal surface of repair implant 60. Overtube 70 and advancement tube 72 are pushed so that locking mechanism 74 and lock 80 engage implant-penetrating element 47a of anchor 49. As tubes 70 and 72 are pushed, locking mechanism 74 is pushed toward implant 60, and mechanism 74 in turn, pushes on annular distal portion 82 of lock 80 in order to slide lock 80 distally and around proximal restraining element 53a. As annular distal portion 82 is pushed, prongs 84 slide along proximal restraining element 53a (FIG. 6A).

Typically, in their resting state, the proximal portions of prongs 84 are aligned in a manner in which they form a circle at their cross-section having a longest dimension measured at a cross-section (measured at a plane that is perpendicular to the longitudinal axis along which length L1 of implant 60 is measured) of between 0.25 mm and 0.6 mm, (e.g., 0.45 mm) and a greatest cross-sectional area of between 0.05 mm^2 and 0.28 mm^2, e.g., 0.16 mm^2. It is to be noted that the proximal portions of prongs 84 are aligned in a manner in which they form a circle by way of illustration and not limitation, and that proximal portions of prongs 84 may be shaped so as to assume any given shape at their cross-section having a greatest cross-sectional area during the resting state of between 0.05 mm^2 and 0.28 mm^2, e.g., 0.16 mm^2. Since proximal restraining element 53a has a longest dimension at its cross-section of between 0.3 mm and 0.75 mm, as prongs 84 are advanced distally over proximal restraining element 53a proximal restraining element 53*a* pushes the proximal portions of prongs 84 radially such that the proximal portions of prongs 84 expand from their resting state to assume a greatest cross-sectional area of between 0.33 and 0.64 mm^2, i.e., a longest dimension at the cross-section of between 0.65 mm and 0.9 mm. As the proximal portions of prongs 84 are radially pushed, their collective cross-sectional area is larger than the greatest cross-sectional area of proximal restraining element 53*a*.

In response to continued pushing of lock 80 by locking mechanism 74, lock 80 slides distally until the respective proximal ends of each prong 84 are disposed distally to the distal end of proximal restraining element 53*a* (shown in FIG. 6B). Since the greatest cross-sectional area of post 52*a* (i.e., between 0.03 mm^2 and 0.2 mm^2) is smaller than the greatest cross-sectional area of proximal restraining element 53*a* (i.e., between 0.07 mm^2 and 0.44 mm^2), the proximal portions of prongs 84 radially collapse around post 52*a* to assume a greatest cross-sectional area that is smaller than the greatest cross-sectional area of proximal restraining element 53*a*. Since the greatest cross-sectional area of proximal restraining element 53*a* is larger than the greatest collective cross-sectional area of the proximal portions of prongs 84 in their resting state and as they surround post 52*a*, prongs 84 are restricted from moving proximally because they have collapsed around post 52*a*. That is, when lock 80 moves proximally along post 52*a*, the proximal end portions of prongs 84 abut against the distal end of proximal restraining element 53*a*. In such a manner, proximal restraining element 53*a*, restrains prongs 84 of lock 80 from sliding proximally, and thereby proximal restraining element 53*a*, together with lock 80, restrain implant 60 from sliding proximally away from anchor 49 and from annulus 25. In such a manner, post 52*a* functions as a protrusion which protrudes into a plane defined by implant 60, and the distal portion of proximal restraining element 53*a* functions as a shelf which facilitates restricting of proximal potion of the implant along the protrusion. As described herein above with reference to the cross-sectional area of proximal restraining element 53*a* (measured at a plane that is perpendicular to the longitudinal axis along which length L1 of implant 60 is measured), the shelf has a transverse cross-sectional length (i.e., the cross-sectional area, as described hereinabove), that is larger than a transverse cross-sectional length of implant-penetrating element 47*a*.

Additionally, as lock 80 is pushed distally, annular distal portion 82 pushes against a portion of implant 60. Responsively, implant 60 pushes against annular distal portion 82 so as to (1) create pressure between the proximal portions of prongs 84 and the distal end of proximal restraining element 53*a*, and (2) lock 80 in place with respect to proximal restraining element 53*a* in order to restrain implant 60 from sliding proximally.

FIG. 7 shows the decoupling of lock holder 73 from lock 80 and from anchor 49. Overtube 70 is retracted proximally in order to expose arms 75 and 77 of lock holder 73. Once arms 75 and 77 are exposed from within overtube 70, they expand radially, as shown, and respective portions of annular distal portion 82 of lock 80 are freed from within slots 81 and 83 of arms 75 and 77, respectively. Overtube 70, advancement tube 72, and lock holder 73 are then retracted through sheath 34 along cord 54.

Reference is now made to FIGS. 2C and 7. Once lock 80 is locked in place between implant 60 and proximal restraining element 53*a* of anchor 49, cord 54 is clipped distally to proximal end portion 59 thereof so as to create free ends of cord 54. A first free end of cord 54 is then pulled so that the second free end is pulled through advancement tube 72 and toward anchor 49. In response to continued pulling of the first free end of cord 54, the second end of cord 54 is pulled through passage 56 of proximal restraining element 53*a* until cord 54 is decoupled from anchor 49. The physician continues to pull on the first free end of cord 54 until the second free end is once again exposed from within tube 72, and thereby cord 54 is extracted from within the body of the patient.

FIG. 7 shows the decoupling of lock holder 73 of locking mechanism 74 from one of the eight anchors 49 around annulus 25. It is to be noted that the method for the locking in place of implant 60 via anchors 49 and locks 80 (as described hereinabove with reference to FIGS. 5A-B, 6A-B, and 7) is applied to every anchor 49 implanted along annulus 25. FIG. 7 shows implant 60 comprising a partial, open, non-continuous ring as described in U.S. patent application Ser. No. 12/341,960 to Cabiri (which published as 2010/0161047, which issued as U.S. Pat. No. 8,241,351, and which is incorporated herein by reference), by way of illustration and not limitation. For example, any suitable tissue repair device known in the art may be anchored to any tissue of the patient via anchor(s) 49. For example, anchors 49 may be implanted in a stomach of the patient and may be used to anchor a gastric bypass ring to the stomach of the patient, in a manner as described hereinabove.

FIGS. 8 and 9 are schematic illustrations of examples of the types of implants 60 that are anchored to annulus 25 via anchors 49, in accordance with respective applications of the present invention. FIG. 8 shows implant 60 comprising a partial, open, non-continuous annuloplasty ring by way of illustration and not limitation. FIG. 9 shows a system 110 in which implant 60 comprises a full annuloplasty ring by way of illustration and not limitation. As described hereinabove implants 60, as shown in FIGS. 8 and 9, are shown by way of illustration and not limitation and that any suitable tissue-remodeling device or implant may be anchored to tissue of the patient using anchor(s) 49.

Figure 10:
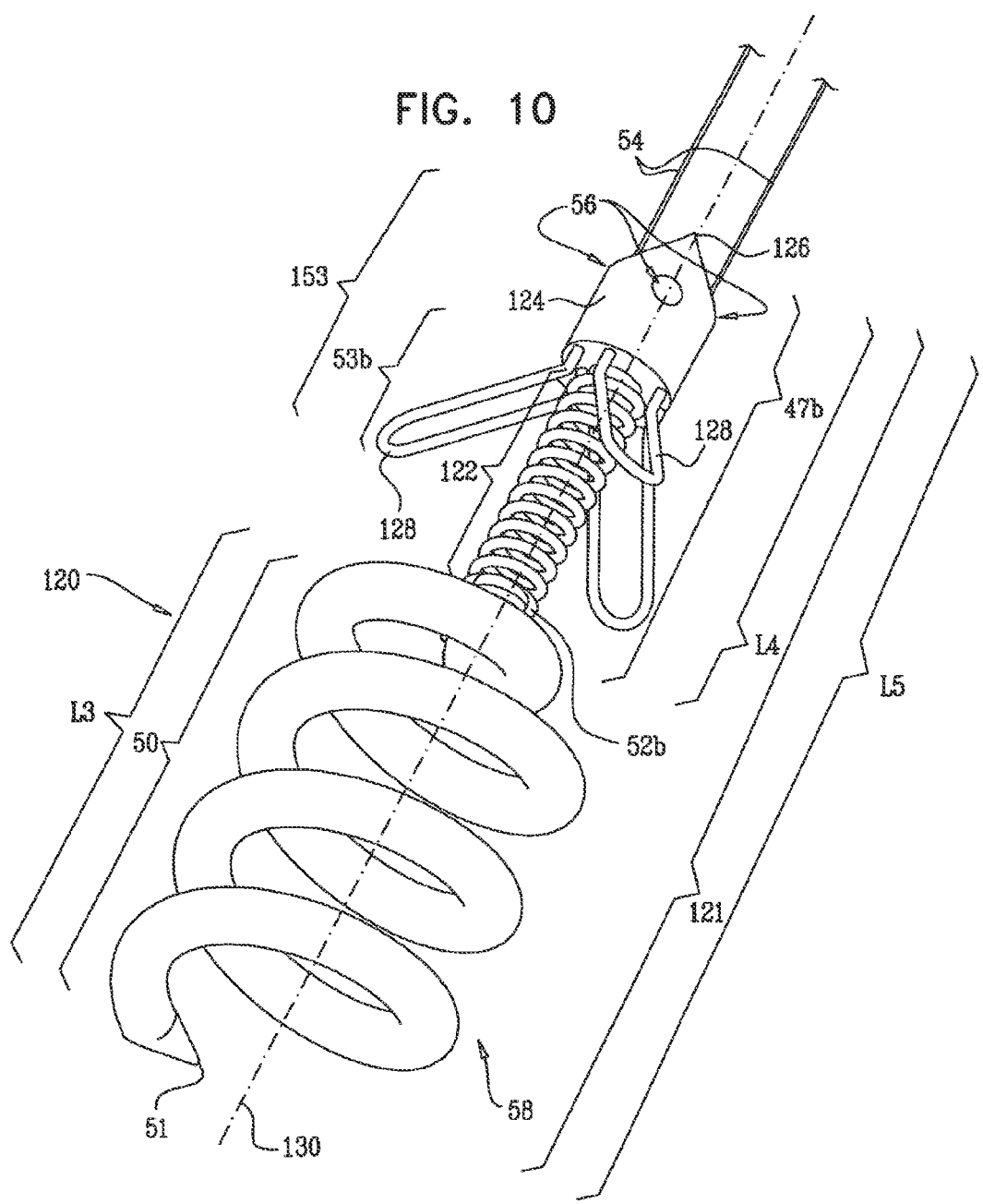
FIG. 10 is a schematic illustration of a tissue anchor for receiving a valve-repair implant, in accordance with another application of the present invention.

Reference is now made to FIG. 10, which is a schematic illustration of a system 120 comprising a tissue anchor 121 comprising a distal tissue coupling element 50 and a proximal implant-penetrating element 47*b*, in accordance with some applications of the present invention. Implant-penetrating element 47*b* comprises a proximal elastic portion comprising a tension spring 122 and a proximal restraining element 53*b* comprising radially-expandable anchor arms 128. Implant-penetrating element 47*b* comprises a proximal portion 124 shaped to define a pointed tip 126 for penetrating an implant (e.g., a tissue-repair implant 60) and facilitating passage of the implant over implant-penetrating element 47*b*. Typically, proximal portion 124, pointed tip 126, and arms 128 together form and function as a barb 153. A proximal elastic portion comprises a tension spring 122 (i.e., implant-penetrating element 47*b*), as shown by way of illustration and not limitation, and has a length L4 of between 3 mm and 5 mm, e.g., 4 mm, when spring 122 is relaxed. Radially-expandable arms 128 are compressible and expandable along a longitudinal axis 130 of anchor 121. Distal tissue coupling element 50 comprises a distal tissue-penetrating tip 51 and is shaped to define helical tissue anchor 58 by way of illustration and not limitation, e.g., tissue coupling element 50 may comprise any suitable tissue anchor known in the art (e.g., as is shown hereinbelow in FIGS. 19 and 20).

It is to be noted that proximal implant-penetrating element 47*b* of anchor 121 is similar in function to proximal implant-penetrating element 47*a* of anchor 49 in that both proximal implant-penetrating elements 47*a* and 47*b* function to receive and facilitate coupling of the implant to the tissue anchor. It is to be further noted that proximal restraining element 53*b* of anchor 121 is similar in function to proximal restraining element 53a of anchor 49 in that both proximal restraining elements 53a and 53b function to restrain the implant from sliding proximally and separating from respective implant-penetrating elements 47a and 47b.

As described hereinabove, distal tissue coupling element 50 has length L3 of 2-8 mm, e.g., 4 mm. Thus, for some applications, anchor 121 has a total length L5 of 5-13 mm.

The elastic portion is shown in FIG. 10 when spring 122 is in its relaxed, resting state. In this relaxed state of spring 122, the elastic portion has a length of between 3 and 5 mm. Spring 122 is configured to be pulled during one stage of implantation of the tissue-repair device. During such pulling, spring 122 is under load and assumes a greater length when under load than when in its relaxed state.

The proximal portion of implant-penetrating element 47b is shaped so as to define one or more passages 56 therethrough. It is to be noted that only one opening of one passage 56 is shown in the configuration as shown in FIG. 10, and that cord 54 passes through passage 56 on the sides of proximal portion 124. Cord 54 is removably coupled to anchor 121 by being passed through passage 56 (as described hereinabove with reference to anchor 49) and functions to facilitate guiding of the valve-repair implant toward tissue anchor 121 implanted at annulus 25. As described hereinabove, passage 56 has at least two openings that are within 1 mm, e.g., 0.5 mm, of a proximal end of implant-penetrating element 47b.

The distal portion of implant-penetrating element 47b comprises a post 52b which couples distal tissue coupling element 50 to the elastic portion. Post 52b in such an application has a height of between 0.2 mm and 0.4 mm. Anchor 121, comprising distal tissue coupling element 50 and implant-penetrating element 47b, has a length measured along axis 130 of 6-12 mm, e.g., 10 mm. Implant-penetrating element 47b has a length measured along axis 130 of 4-10 mm, e.g., 5.5 mm. Distal tissue coupling element 50 has a length measured along axis 130 of 2-8 mm, e.g., 4 mm. For some applications, post 52b includes spring 122, and in such an application, post 52b has a length of between 1 and 7 mm.

FIG. 11A shows a plurality of tissue anchors 121 implanted along annulus 25, in accordance with some applications of the present invention. Each anchor 121 is reversibly coupled to an elongate delivery tool (not shown for clarity of illustration) and is transcatheterally advanced via the tool toward annulus 25. The delivery tool facilitates corkscrewing of helical tissue anchor 58 into tissue of the annulus. For applications in distal tissue coupling element 50 comprises any other tissue coupling anchor, the delivery tool facilitates coupling of anchor 121 to annulus 25 by advancing distal tissue coupling element 50 into the tissue of annulus 25.

Each anchor 121 is implanted in a manner in which a proximal end of tissue coupling element 50 is disposed within tissue of annulus 25 and a distal end portion of spring 122 is disposed proximally to the surface of annulus 25, as shown in the enlarged image of tissue anchor 121 of FIG. 11A. For some applications of the present invention, delivery tool 42, as described hereinabove with reference to FIGS. 2A-C may be reversibly coupled to each anchor 121 and facilitate implantation of each anchor 121. In such an application, arms 128 of implant-penetrating element 47b are compressed within slit 48 of manipulator 44 of tool 42.

Once tissue anchor 121 is implanted, cord 54 remains coupled to anchor 121, as described hereinabove with reference to the cord 54 coupled to tissue anchor 49. It is to be noted that although eight anchors 121 are implanted around annulus 25 by way of illustration and not limitation, any suitable number of anchors 121 may be implanted along annulus 25 according to the needs of a given patient, e.g., depending on the level of distention and relaxation of the annulus of a given patient.

Figure 11B:
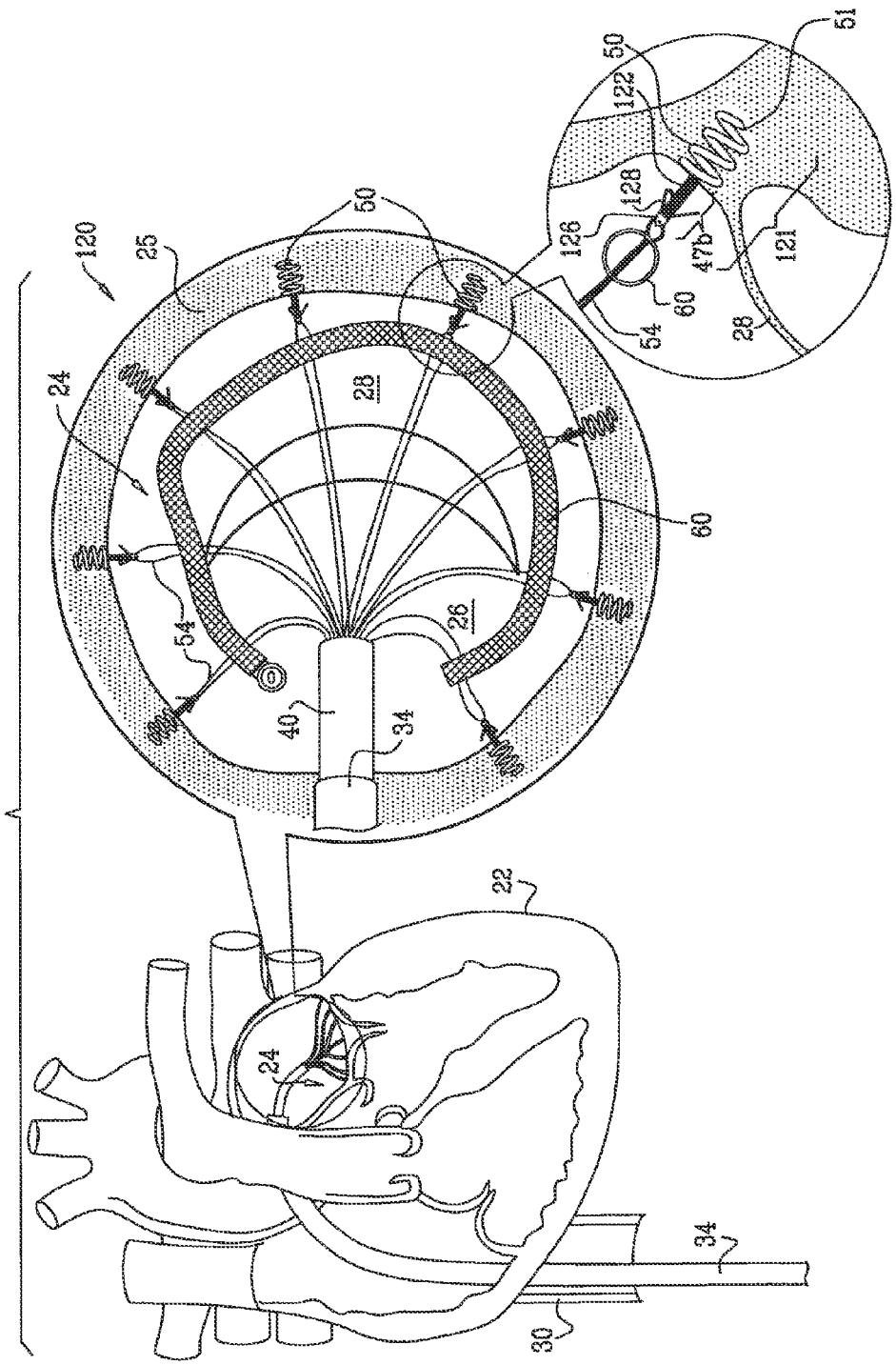

Reference is now made to FIG. 11B, which is a schematic illustration of a tissue-repair implant 60 being advanced along cords 54 toward annulus 25 of the mitral valve of the patient. As shown, repair implant 60 comprises a non-continuous, open, partial annuloplasty ring, by way of illustration and not limitation. It is to be noted that any valve repair implant, e.g., a full annuloplasty ring, a partial annuloplasty ring, or a prosthetic valve, may be advanceable along cords 54. The partial, open ring of repair implant 60 may be implemented using any one of the techniques described in U.S. patent application Ser. No. 12/341,960 to Cabiri, which published as 2010/0161047, which issued as U.S. Pat. No. 8,241,351, and which is incorporated herein by reference.

Implant 60 is advanced along cords 54, in a manner as described hereinabove with reference to FIGS. 2C and 4. A pushing tool (not shown for clarity of illustration) is used to push implant 60 through catheter 40 and toward annulus 25. Implant 60 is pushed until respective portions of a distal surface of implant 60 contact each pointed tip 126 of proximal portion 124 of implant-penetrating element 47b.

Figure 11C:
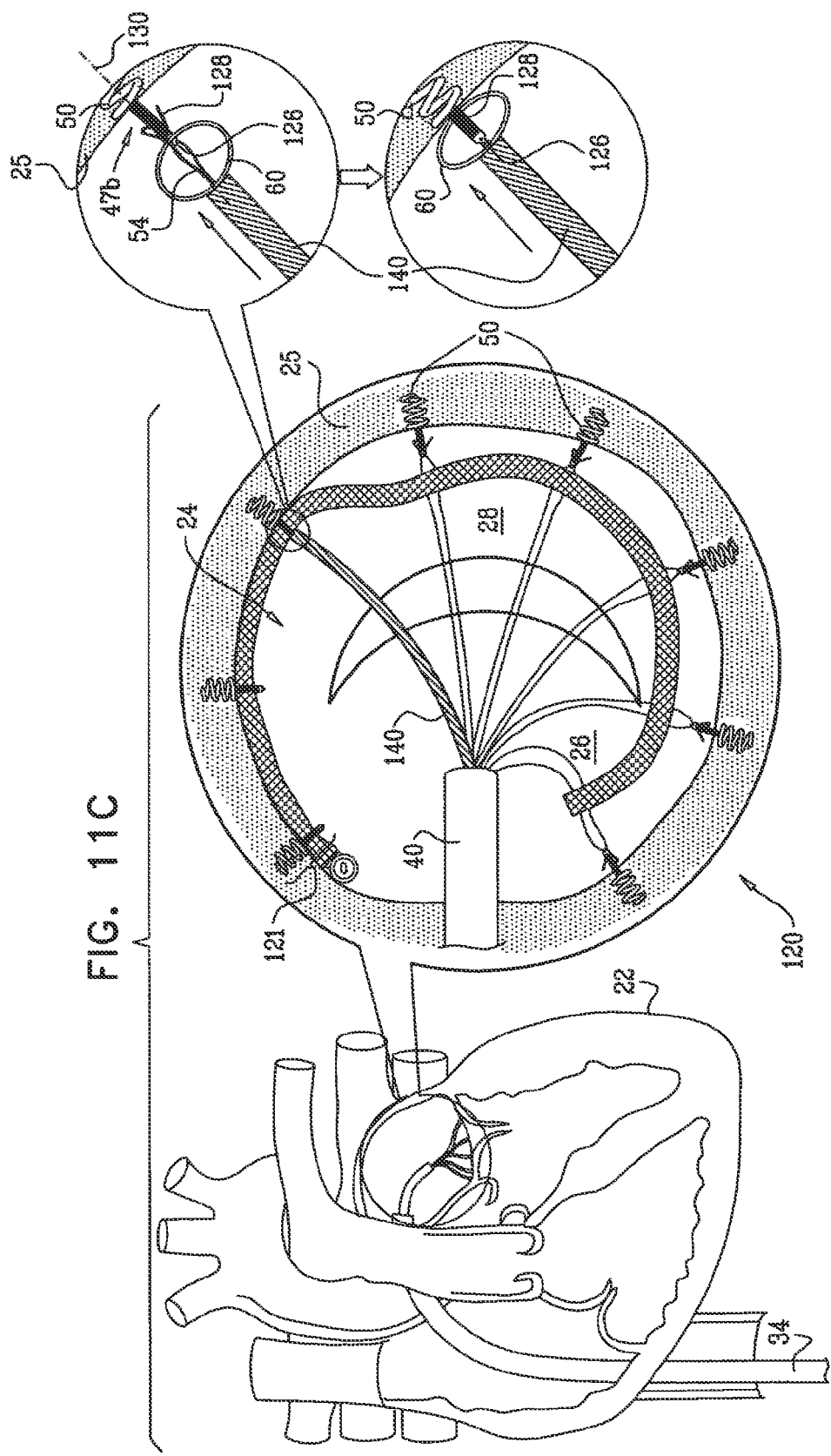

FIG. 11C shows a pushing tool 140, as described hereinabove with reference to FIG. 11B, that pushes respective portions of implant 60 such that they are engaged by each implant-penetrating element 47b of anchors 121, in accordance with some applications of the present invention. Pushing tool 140 is advanced along a respective cord 54, as shown, and toward a portion of implant 60. The physician uses pushing tool 140 to push on the proximal surface of implant 60 such that the distal surface of implant 60 is punctured by pointed tip 126 of implant-penetrating element 47b. Continued pushing of pushing tool 140: (1) advances a portion of implant 60 around arms 128 and along the elastic portion and spring 122 of implant-penetrating element 47b, and thereby (2) facilitates coupling of the portion of implant 60 to anchor 121. As implant 60 is pushed, spring 122 compresses along axis 130 and provides flexibility to system 120, as implant 60 is anchored to annulus 25.

Following the puncturing of the distal surface of the portion of implant 60 by pointed proximal tip 126 of implant-penetrating element 47b, an opening is created at the distal surface of implant 60 for passage therethrough of a proximal portion of implant-penetrating element 47b. As implant 60 is pushed along implant-penetrating element 47b, the proximal portion is disposed within the lumen of implant 60, as shown in the enlarged image of FIG. 11C. The opening at the distal surface of implant 60 that is created by puncturing the material of implant 60 closes around and radially compresses radially-expandable arms 128 as the proximal portion of implant-penetrating element 47b passes through implant 60 in conjunction with the pushing of implant 60 (as shown in the enlarged cross-sectional images of implant 60 being coupled to anchor 121). Radially-expandable arms 128 are compressed such that they align alongside spring 122 as the portion of implant 60 is pushed along implant-penetrating element 47b. Responsively to continued pushing of the portion of implant 60 by tool 140, pointed proximal tip 126 of implant-penetrating element 47b punctures a proximal surface of the portion of implant 60 from within the lumen of implant 60, and proximal tip 126 emerges proximally to the proximal surface of implant 60.

Figure 11D:
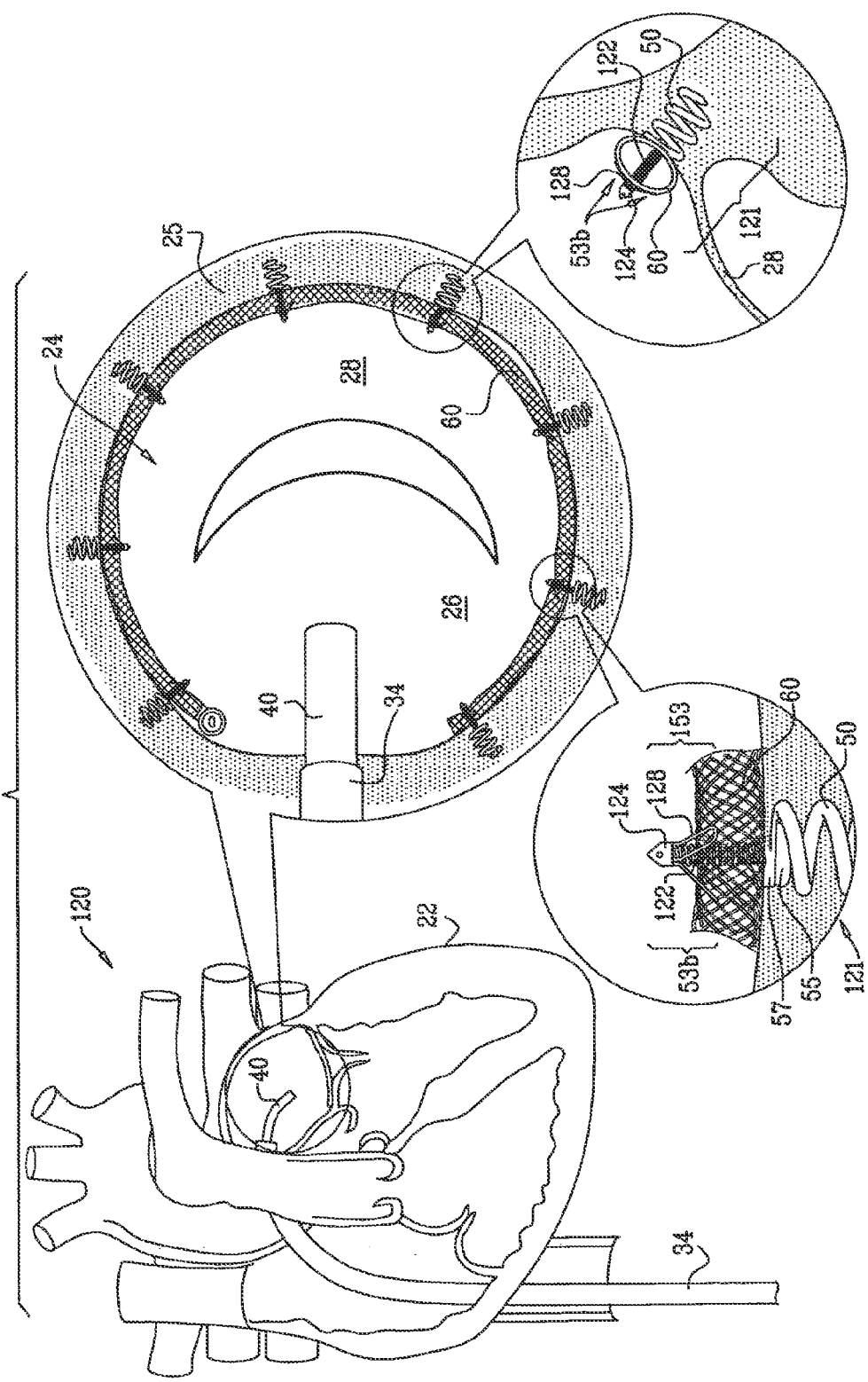

Reference is now made to FIG. 11D, which is a schematic illustration of the locking in place of the portion of implant 60 at a given location along annulus 25 via arms 128 of anchor 121, in accordance with some applications of the present invention. As described hereinabove, responsively to continued pushing of the portion of implant 60 by tool 140, pointed tip 126 of implant-penetrating element 47b punctures and creates an opening at the proximal surface of implant 60 and emerges from within the lumen of implant 60 proximally to the upper surface of implant 60. Responsively to continued pushing of the portion of implant 60 by tool 140, implant 60 slides along implant-penetrating element 47b such that respective distal ends of arms 128 emerge from within the lumen of implant 60 and through the opening at the proximal surface of the portion of implant 60. Once arms 128 are freed from within the lumen of the portion of implant 60 (i.e., are no longer radially compressed by the lumen of the portion of implant 60 and/or the respective openings at the proximal and distal surfaces of the portion of implant 60), arms 128 expand radially, as shown in the enlarged images of FIG. 11D. Arms 128 are configured to radially compress and expand between 0 and 30 degrees with respect to axis 130 of anchor 121. Arms 128 expand such that (1) the proximal ends thereof collectively form a perimeter that is larger than the perimeter of the external surface of implant 60, and (2) arms 128 lock in place around implant 60 to restrict proximal movement of implant 60.

Reference is now made to FIGS. 11C-D. Arms 128 expand around the external surface of implant 60 and thus function as proximal restraining element 53b to restrain proximal sliding of implant 60 along implant-penetrating element 47b and decoupling of implant 60 from anchor 121 (FIG. 11D). Once arms 128 expand and lock in place the portion of implant 60 to annulus 25 via anchor 121, pushing tool 140 is extracted from the body of the patient through catheter 40. Spring 122 is thus no longer compressed responsively to the pushing force of implant 60 applied by tool 140, and spring 122 relaxes and returns to its resting state (FIG. 11D). As shown in FIG. 11C, following the coupling of respective portions of implant 60 to anchors 121, each cord 54 coupled to the respective anchor 121 is cut, as described hereinabove with reference to FIG. 2B, and decoupled from the respective anchor 121. Typically, but not necessarily, each cord 54 is decoupled from anchor 121 immediately following the coupling of the respective portion of implant 60 to each anchor 121 (as shown in FIG. 11C). Alternatively, cords 54 remain coupled to respective anchors 121 until the entire implant 60 is coupled to annulus 25 via anchors 121.

In some embodiments, in conjunction with the pushing of implant 60 by tool 140, cord 54 is pulled taut so as to apply load to spring 122 such that it expands to a length greater than its length during the resting state of spring 122. The pulling of spring 122 helps pull arms 128 through the lumen of implant 60 such that they emerge from within the lumen of implant 60. Once arms 128 emerge from within the lumen of implant 60, cord 54 is no longer pulled, and spring 122 returns to its resting state in order to allow arms 128 to rest against an external proximal surface of implant 60 and restrict proximal movement of implant 60 along implant-penetrating element 47b. Thus, arms 128 function as proximal restraining element 53b, and arms 128 together with portion 124 and tip 126 function as barb 153b.

Reference is again made to FIG. 11C, which shows, by way of illustration and not limitation, implant 60 being coupled to anchors 121 in a systematic order beginning from the leftmost anchor 121, (i.e., disposed at 10 o'clock) and moving clockwise in series from anchor to anchor. It is to be noted that implant 60 may be coupled to anchors 121 in any suitable order (i.e., not in series from anchor to anchor), in accordance with the protocol of the operating physician.

Reference is now made to FIGS. 12-14, which are schematic illustrations of a system 200 for implanting anchors 49 and 121 described hereinabove in an open-heart or minimally-invasive procedure, in accordance with some applications of the present invention. System 200 comprises a tool body 202 and proximal handle portions 204 and 206. Tool body 202 comprises an outer tube shaft 210 and an inner tube shaft 212 (FIG. 14). Inner tube shaft 212 functions similarly to the elongate tube shaft of delivery tool 42, as described hereinabove with reference to FIGS. 2A-C. The distal end of tube shaft 212 is coupled to manipulator 44 that is described hereinabove with reference to FIGS. 2A-C. Manipulator 44 is reversibly coupled to anchor 49, as described hereinabove. It is to be noted that although FIGS. 12-14 show manipulator 44 coupled to anchor 49, manipulator 44 may also be coupled to anchor 121, in a manner as described hereinabove with reference to FIG. 11A. The proximal end of inner tube shaft 212 is coupled to handle portion 206 of tool body 202. For some applications, handle portion 206 is rotatable along an axis 230 of tool body 202 in order to (1) rotate inner tube shaft 212 and, thereby, rotate manipulator 44, and thereby (2) facilitate corkscrewing of distal tissue coupling element 50 of anchor 49 into tissue of annulus 25. Alternatively, the entire tool body 202 is rotated about axis 230 of tool body 202 in order to rotate distal tissue coupling element 50 of anchor 49 and facilitate corkscrewing of distal tissue coupling element 50 of anchor 49 into tissue of annulus 25. In either application, following the corkscrewing of distal tissue coupling element 50 into tissue of annulus 25, anchor 49 is decoupled from manipulator 44, as described hereinabove with reference to FIG. 2B, and thereby decoupled from tool body 202.

As shown in FIG. 14, inner tube shaft 212 is housed within a lumen of outer tube shaft 210. Inner tube shaft 212 and handle portions 204 and 206 are each shaped to provide a lumen for passage therethrough of cord 54 coupled to anchor 49. Tool body 202 is shaped so as to provide (1) a proximal opening 214 for passage therethrough of cord 54, and (2) a distal opening 216 for passage therethrough of anchor 49. Once distal tissue coupling element 50 of anchor 49 is corkscrewed into tissue of annulus 25 and anchor 49 is decoupled from manipulator 44, tool body 202 is slid proximally along cord 54 leaving anchor 49 and a portion of cord 54 in heart 22 of the patient.

Figure 15:
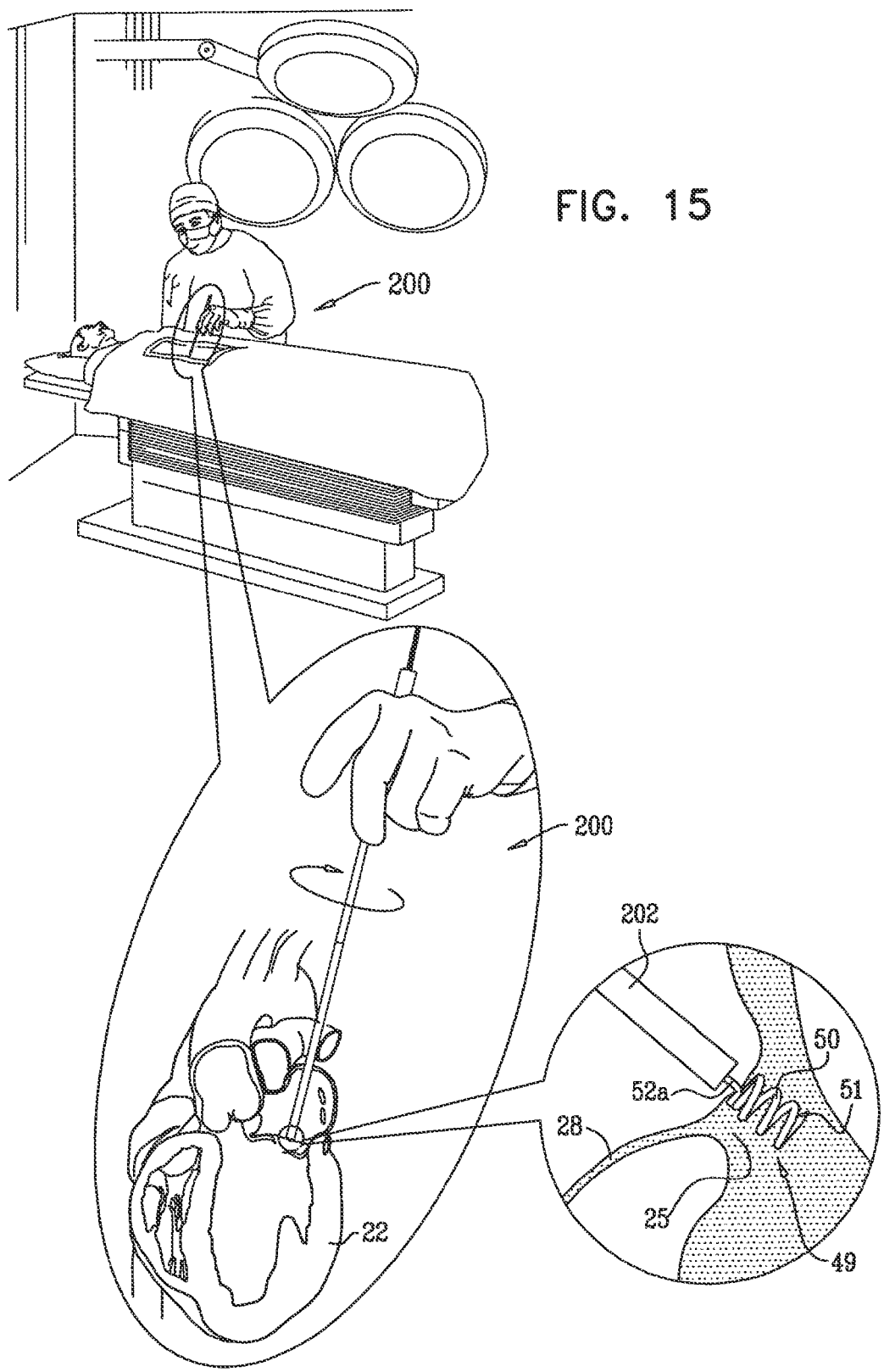
FIGS. 15-18 are schematic illustrations of the implantation and locking of the valve-repair implant during the minimally-invasive or open-heart procedure, in accordance with some applications of the present invention.

FIG. 15 shows system 200 being used to implant anchor 49 in heart 22 of the patient, in accordance with some applications of the present invention during an open-heart or minimally-invasive procedure. In these procedures, an incision is created in heart 22 at the left atrium to provide a passage for the distal end portion of tool body 202 to access an atrial surface of the mitral valve. As shown, tool body 202 (or tube shaft 212) is rotated in order to facilitate corkscrewing of distal tissue coupling element 50 of anchor 49 into tissue of annulus 25. As described hereinabove, pointed distal tip 51 punctures tissue of annulus 25 in order to facilitate corkscrewing of distal tissue coupling element 50 into tissue of annulus 25.

Figure 16:
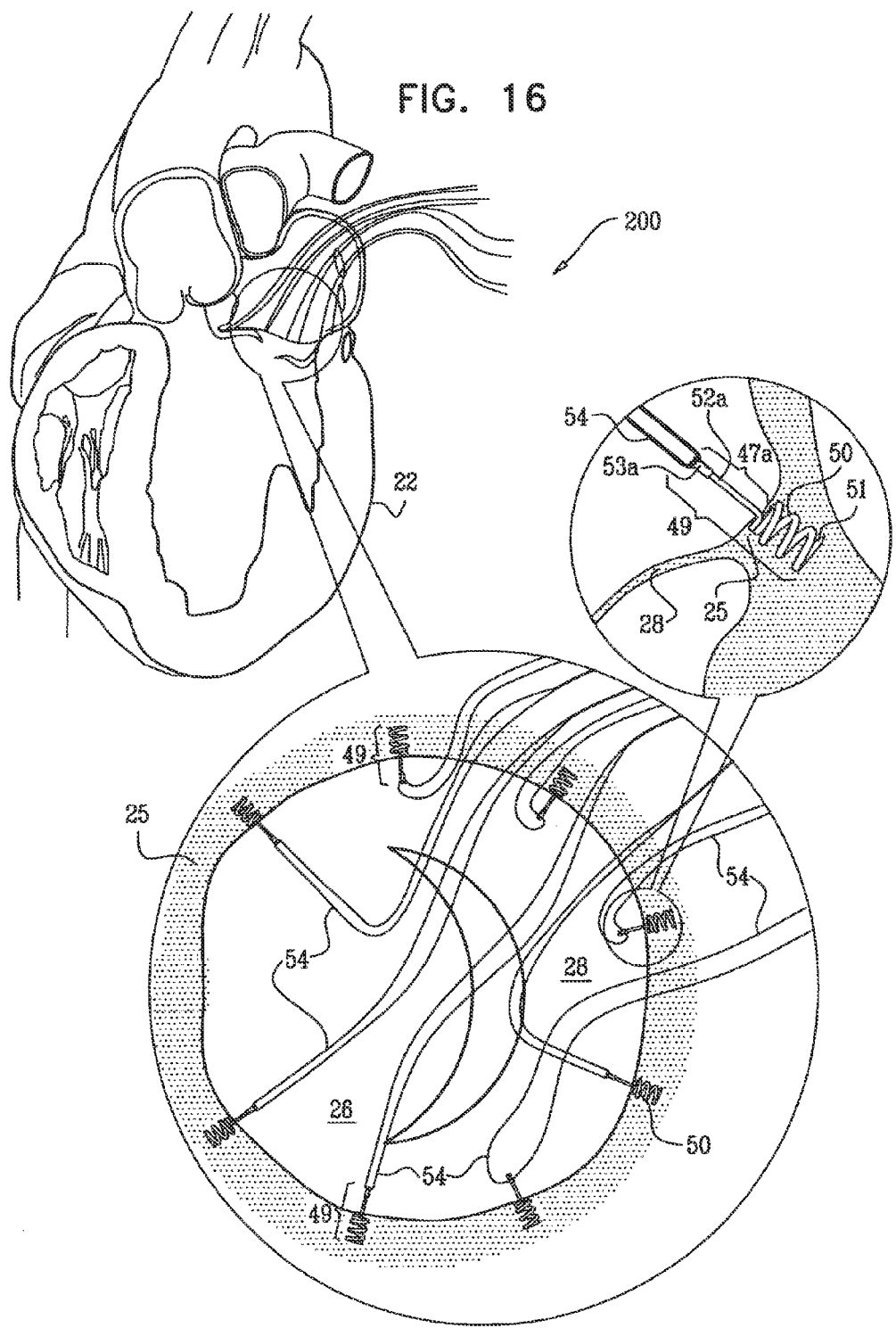

FIG. 16 shows a plurality of anchors 49 implanted along annulus 25 following the corkscrewing of distal tissue coupling element 50 of each anchor 49 into tissue of annulus 25, as facilitated by tool body 202 of system 200 described hereinabove with reference to FIGS. 12-14, in accordance with some applications of the present invention. It is to be noted that anchors 121, as described hereinabove with reference to FIGS. 10 and 11A-D, may be implanted along annulus 25 using tool body 202 of system 200. Following the implantation of each anchor 49 via tool body 202, respective cords 54 remain coupled to each anchor 49. The proximal end portions of each cord 54 are accessible outside the body of the patient.

As shown, each distal tissue coupling element 50 is disposed within tissue of annulus 25, and each proximal restraining element 53a and post 52a of each anchor 49 extend proximally from the proximal surface of annulus 25. Each implant-penetrating element 47a comprising proximal restraining element 53a and post 52a is thus accessible by any tissue-repair implant 60 advanced theretoward along cord 54 reversibly coupled to proximal restraining element 53a.

Figure 17:
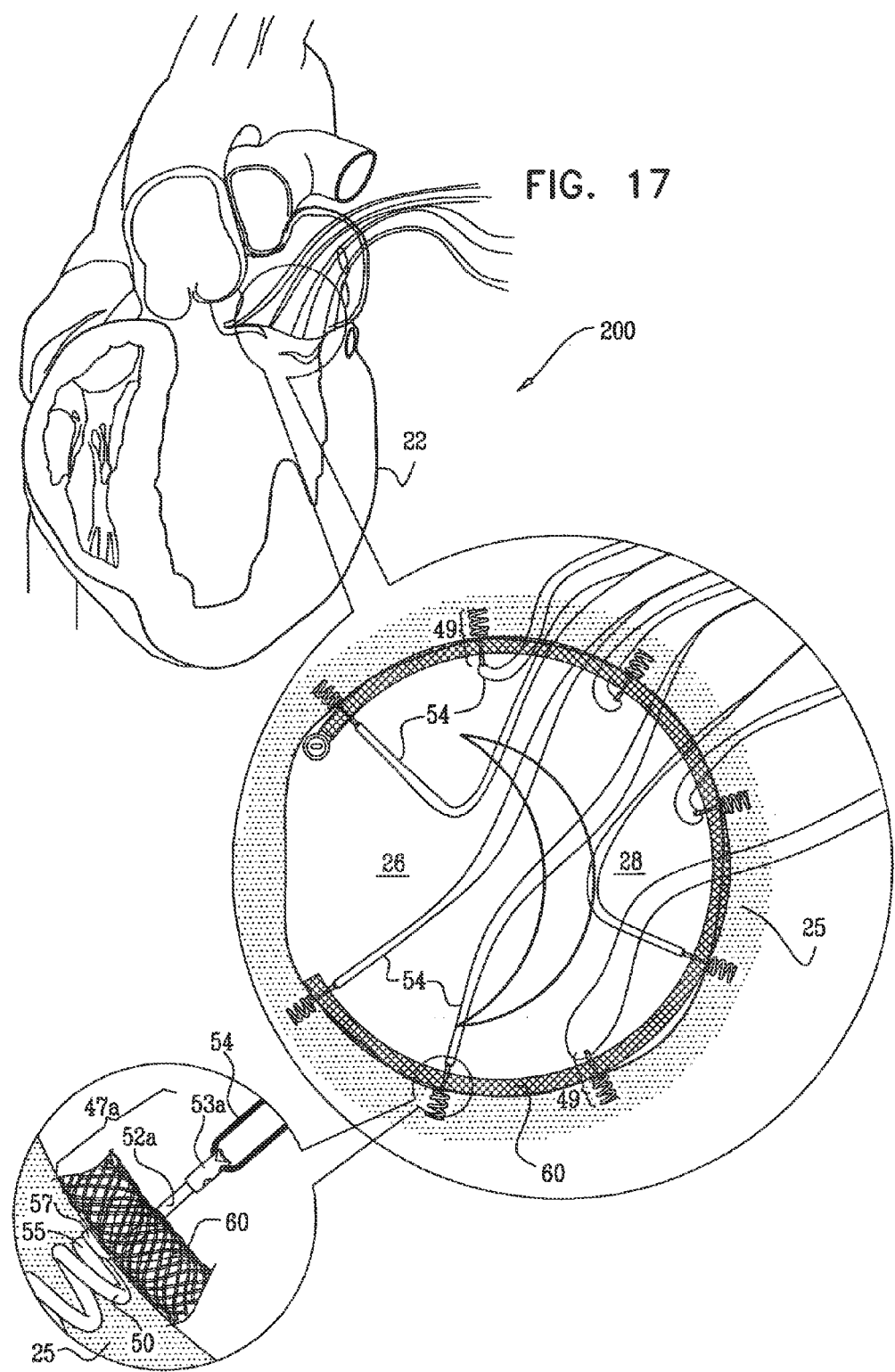

FIG. 17 shows tissue-repair implant 60, as described hereinabove, coupled to annulus 25 via anchor 49, in accordance with some applications of the present invention. As described hereinabove, implant 60 is advanced along cords 54 toward tissue of annulus 25. A tool may be used to advance respective portions of implant 60 along each cord 54. Alternatively, during an open-heart procedure, the physician uses his or her fingers to push respective portions of implant 60 along each cord 54. As shown in the enlarged image of FIG. 17, a portion of implant 60 is coupled to anchor 49 in a manner in which: (1) the distal surface of the portion of implant 60 contacts the proximal surface of annulus 25, (2) a distal portion of post 52a is disposed within the lumen of implant 60, and (3) a distal end of proximal restraining element 53a is disposed proximally to a proximal surface of the portion of implant 60. As shown, cords 54 remain coupled to anchors 49 following the coupling of the respective portions of implant 60 to implant-penetrating element 47a of each anchor 49.

Figure 18:
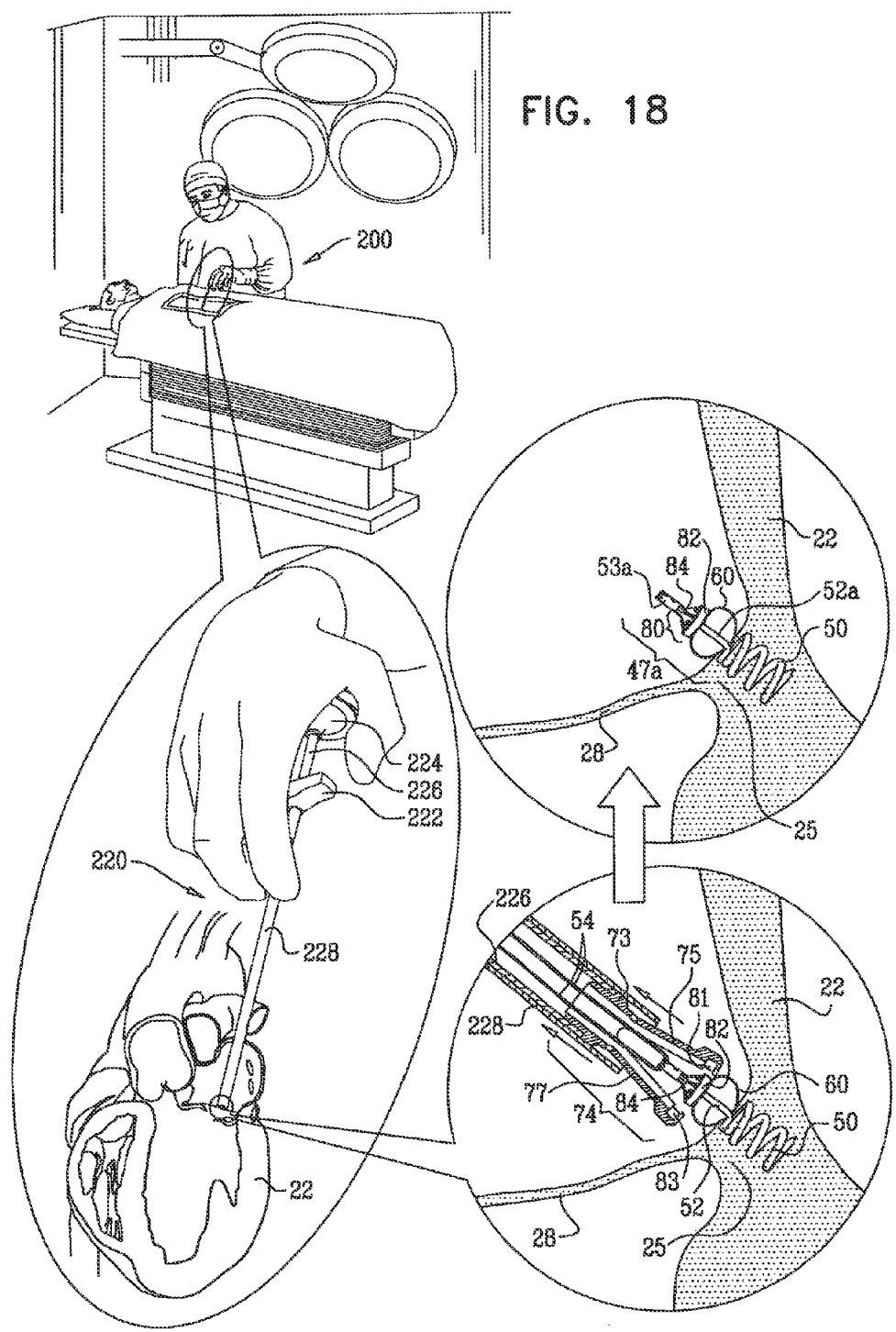

FIG. 18 shows a tool system 220 for coupling a respective lock 80 to a portion of implant-penetrating element 47a that is distal to proximal restraining element 53a of each anchor 49, in accordance with some applications of the present invention. Tool system 220 comprises an outer tube shaft 228 which is shaped to provide a lumen for slidable movement of an inner tube shaft 226. As shown in the enlarged cross-sectional image of FIG. 18, tube shaft 226 is shaped so as to provide a lumen for passage therethrough of cord 54 in order to facilitate sliding of tool system 220 along cord 54 and toward anchor 49.

A distal end of inner tube shaft 226 is coupled to locking mechanism 74 comprising lock holder 73, as described hereinabove with reference to FIGS. 5A-B. Thus, inner tube shaft 226 functions similarly to advancement tube 72 (as described hereinabove with reference to FIGS. 5A-B) in order to advance locking mechanism distally through outer tube shaft 228. Outer tube shaft 228 functions similarly to overtube 70 (as described hereinabove with reference to FIGS. 5A-B) in order to surround radially-expandable arms 75 and 77 of locking mechanism 74 and maintain arms 75 and 77 in a compressed state within a distal portion of shaft 228 during a resting state of system 220. As described hereinabove, lock holder 73 of locking mechanism 74 is reversibly coupled to a lock 80 which locks in place a portion of implant 60 to annulus 25 via anchor 49.

A proximal portion of inner tube shaft 226 is coupled to a first engageable element 222, while a proximal end of outer tube shaft 228 is coupled to a second engageable element 224. First and second engageable elements 222 and 224 are engageable by the hand of the operating physician. Tool system 220 is spring-loaded so as to facilitate controlled displacement of second engageable element 224 from first engageable element 222. Responsively to pulling of second engageable portion 224 away from first engageable element 222, outer tube shaft 228 slides proximally along inner tube shaft 226.

Prior to the pulling of second engageable element 224, the operating physician pushes the entire tool system 220 (i.e., without pulling second engageable element 224 away from first engageable element 222) such that (1) the distal end of outer tube shaft 228 contacts the proximal surface of implant 60, and (2) lock 80 is pushed along proximal restraining element 53a and engages post 52a, in a manner as described hereinabove with reference to FIGS. 5A-B, 6A-B, and 7. The physician then pulls second engageable element 224 away from first engageable element 222. In response to the pulling of engageable element 224 (i.e., a pulled state of system 220), tube shaft 228 is pulled and a distal portion of lock holder 73 is exposed distally to the distal end of outer tube shaft 228. Arms 75 and 77 are freed from within a distal end portion of outer tube shaft 228 and radially expand. Annular distal portion 82 of lock 80 is then freed from within slots 81 and 83 of arms 75 and 77, respectively, and lock 80 is decoupled from locking mechanism 74 and tool system 220. Once lock 80 is locked in place between implant 60 and proximal restraining element 53a, cord 54 is clipped distally to proximal end portion 59 thereof so as to create free ends of cord 54, and cord 54 is extracted from within the body of the patient, as described hereinabove with reference to FIGS. 2C and 7.

As shown in the enlarged cross-sectional images of FIG. 18, a distal portion of post 52a couples implant 60 to anchor 49 by being disposed within the lumen of implant 60 between a first opening of implant 60 at a distal surface thereof and a second opening of implant 60 at a proximal surface thereof.

Reference is now made to FIG. 19, which is a schematic illustration of a system 320 comprising a tissue anchor 321 that is similar to tissue anchor 49, as described hereinabove, with the exception that distal tissue coupling element 50 comprises an expandable tissue anchor 322 which comprises one or more, e.g., a plurality, of radially-expandable prongs 326, in accordance with some applications of the present invention. Prongs 326 comprise flexible metal, e.g., nitinol or stainless steel, and have a tendency to expand radially, as shown in the left-most image in FIG. 19. Anchors 322 facilitate coupling of tissue anchor 321 to annulus 25 of the native valve, such as the mitral valve or the tricuspid valve, or to any other valve or tissue. Tissue anchor 322 is shaped so as to define a pointed distal tip 324 configured to puncture tissue of annulus 25. As described hereinabove, distal tissue coupling element 50, which, for this application of the present invention comprises tissue anchor 322, has length L3 of 2-8 mm, e.g., 4 mm.

Tissue anchor 322 is coupled to (e.g., welded or otherwise coupled to) post 52a of implant-penetrating element 47a, as described hereinabove. Implant-penetrating element 47a has length L2 of 4-10 mm, e.g., 5.5 mm. Taken together, tissue anchor 321 has length L1 of 6-18 mm, e.g., 10 mm.

In the right-side images of FIG. 19, tissue anchor 322 is shown being implanted into tissue of annulus 25. Pointed distal tip 324 punctures tissue of annulus 25. In response to distal pushing of anchor 321, tissue anchor 322 is pushed within tissue of annulus 25. As anchor 321 is pushed, the force of the tissue of annulus 25 pushes against prongs 326 and compresses prongs 326 inwardly (as shown in the upper-right image). Following the pushing of anchor 321 distally, anchor 321 is pulled slightly proximally (e.g., by pulling on cord 54) in order to enable prongs 326 to expand radially to assume a flower shape and a larger surface area, to restrict proximal motion of anchor 321 in tissue of annulus 25.

Following the implanting of anchor 322 within tissue of annulus 25, post 52a remains disposed proximally to a surface of annulus 25, so that it can puncture and receive the implant, as described hereinabove.

FIG. 20 shows a system 420 comprising a tissue anchor 421 that is similar to tissue anchor 121, as described hereinabove, with the exception that distal tissue coupling element 50 comprises an expandable tissue anchor 322, as described hereinabove with reference to FIG. 19, in accordance with some applications of the present invention. As described hereinabove, distal tissue coupling element 50, which, for this application of the present invention comprises tissue anchor 322, has length L3 of 2-8 mm, e.g., 4 mm. Also, as described hereinabove, anchor 421 comprises a proximal elastic portion which comprises tension spring 122, as shown by way of illustration and not limitation. Implant-penetrating element 47b has a length L4 of between 3 mm and 5 mm, e.g., 4 mm, when spring 122 is relaxed. Thus, for some applications, anchor 421 has a total length L5 of 5-13 mm.

Tissue anchor 421 comprises distal tissue coupling element 50 and proximal implant-penetrating element 47b. As described hereinabove, implant-penetrating element 47b comprises the proximal elastic portion comprising tension spring 122 and proximal restraining element 53b comprising radially-expandable anchor arms 128. Implant-penetrating element 47b comprises a proximal portion 124 shaped to define a pointed tip 126 for penetrating an implant (e.g., a tissue-repair implant 60) and facilitating passage of the implant over implant-penetrating element 47b. Typically, proximal portion 124, pointed tip 126, and arms 128 together form and function as a barb 153.

Reference is now made to FIGS. 19 and 20. For some applications of the present invention, during the delivery of anchors 321 and 421 toward annulus 25, a sheath (not shown) surrounds prongs 326 so as to keep them in a closed state and facilitate atraumatic advancement of prongs 326 toward tissue at annulus 25.

Reference is now made to FIGS. 1A-F, 2A-C, 3-4, 5A-B, 6A-B, 7-10, 11A-D, and 12-20. It is to be noted that systems, methods, and anchors 49, 121, 321, and 421 described herein may be used at any atrioventricular valve, e.g., the mitral valve or the tricuspid valve. It is to be further noted that systems, methods, and anchors 49, 121, 321, and 421 described herein may be implanted at any suitable tissue site (e.g., tissue of a stomach of the patient) in order to facilitate implantation of any suitable implant.

For some applications of the present invention, techniques described herein are practiced in combination with techniques described in one or more of the references cited in the Background section of the present patent application.

Additionally, the scope of the present invention includes applications described in one or more of the following:

PCT Publication WO 06/097931 to Gross et al., entitled, "Mitral Valve treatment techniques," filed Mar. 15, 2006;

U.S. Provisional Patent Application 60/873,075 to Gross et al., entitled, "Mitral valve closure techniques," filed Dec. 5, 2006;

U.S. Provisional Patent Application 60/902,146 to Gross et al., entitled, "Mitral valve closure techniques," filed Feb. 16, 2007;

U.S. Provisional Patent Application 61/001,013 to Gross et al., entitled, "Segmented ring placement," filed Oct. 29, 2007;

PCT Publication WO 08/068756 to Gross et al., entitled, "Segmented ring placement," filed Dec. 5, 2007;

U.S. patent application Ser. No. 11/950,930 to Gross et al., entitled, "Segmented ring placement," filed Dec. 5, 2007, which published as US 2008/0262609;

U.S. patent application Ser. No. 12/435,291 to Maisano et al., entitled, "Adjustable repair chords and spool mechanism therefor," filed on May 4, 2009, which published as US 2010/0161041, which issued as U.S. Pat. No. 8,147,542;

U.S. patent application Ser. No. 12/437,103 to Zipory et al., entitled, "Annuloplasty ring with intra-ring anchoring," filed on May 7, 2009, which published as 2010/0286767, and which issued as U.S. Pat. No. 8,715,342;

PCT Publication WO 10/004546 to Gross et al., entitled, "Annuloplasty devices and methods of delivery therefor," filed on Jun. 15, 2009;

U.S. patent application Ser. No. 12/548,991 to Maisano et al., entitled, "Implantation of repair chords in the heart," filed on Sep. 21, 2009, which published as US 2010/0161042, and which issued as U.S. Pat. No. 8,808,368;

PCT Publication WO 10/073246 to Cabiri et al., entitled, "Adjustable annuloplasty devices and mechanisms therefor," filed Dec. 22, 2009;

U.S. patent application Ser. No. 12/706,868 to Miller et al., entitled, "Actively-engageable movement-restriction mechanism for use with an annuloplasty structure," filed Feb. 17, 2010, which published as US 2010/0211166, and which issued as U.S. Pat. No. 8,353,956;

PCT Patent Application PCT/IL2010/000357 to Maisano et al., entitled, "Implantation of repair chords in the heart," filed May 4, 2010, which published as WO 10/128502; and/or PCT Patent Application PCT/IL2010/000358 to Zipory et al., entitled, "Deployment techniques for annuloplasty ring and over-wire rotation tool," filed May 4, 2010, which published as WO 10/128503.

All of these applications are incorporated herein by reference. Techniques described herein can be practiced in combination with techniques described in one or more of these applications.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with an implant configured to be coupled to cardiac tissue of a patient, the apparatus comprising:

a tissue anchor comprising:
    a distal tissue coupling element configured to couple the tissue anchor to the cardiac tissue of the patient; and
    a proximal implant-receiving element configured to receive at least a portion of the implant and facilitate coupling of the implant to the tissue anchor, the proximal implant-receiving element comprising:
        an implant-restraining element coupled to a portion of the implant-receiving element, the implant-restraining element being configured to restrain the implant from separating from the implant-receiving element, the implant-restraining element comprising a barb configured to restrict proximal movement of the implant along the implant-receiving element, the barb comprising one or more arms that are radially expandable to rest against an external surface of the implant following coupling of the implant to the implant-receiving element.

2. The apparatus according to claim 1, wherein the restraining element comprises a protrusion configured to protrude into a plane of the implant and to couple the implant to the tissue anchor.

3. The apparatus according to claim 2, wherein the protrusion is shaped so as to define a distal shelf that has a transverse cross-sectional length that is larger than a transverse cross-sectional length of the implant-receiving element, the distal shelf being configured to facilitate restricting of proximal motion of the implant along the protrusion.

4. The apparatus according to claim 1, wherein the arms are radially collapsible during at least a portion of the coupling of the implant to the implant-receiving element.

5. The apparatus according to claim 1, wherein the proximal implant-receiving element comprises an elastic portion that is configured to assume a first length when relaxed, and a second, greater length when under load.

6. The apparatus according to claim 5, wherein the elastic portion comprises a tension spring.

7. The apparatus according to claim 5, wherein the proximal implant-receiving element has a length of between 3 and 5 mm when the elastic portion is relaxed.

8. The apparatus according to claim 1, wherein the distal tissue coupling element is shaped so as to define a shape selected from the group consisting of: a helix, a spiral, and a screw shaft.

9. The apparatus according to claim 1, wherein the distal tissue coupling element is shaped so as to define one or more radially-expandable prongs, the prongs being configured to expand and facilitate anchoring of the coupling element and restrict proximal motion of the tissue anchor.

10. The apparatus according to claim 1, further comprising the implant, wherein the implant-receiving element is configured to couple the implant to the anchor.

11. The apparatus according to claim 10, wherein the implant comprises a tissue-repair implant.

12. The apparatus according to claim 10, wherein the implant-restraining element is configured to pass through a portion of the implant.

13. The apparatus according to claim 1, wherein the distal tissue coupling element and the proximal implant-receiving element comprise respective elements that are coupled to one another.

14. The apparatus according to claim 1, wherein the distal tissue coupling element and the proximal implant-receiving element are fabricated from a single piece.

15. The apparatus according to claim 1, wherein the implant-restraining element is coupled to a proximal portion of the implant-receiving element.

16. Apparatus for use with an implant configured to be coupled to cardiac tissue of a patient, the apparatus comprising:
a tissue anchor comprising:
a distal tissue coupling element configured to couple the tissue anchor to the cardiac tissue of the patient; and
a proximal implant-receiving element configured to receive at least a portion of the implant and facilitate coupling of the implant to the tissue anchor, the proximal implant-receiving element comprising:
a post having a length of between 1 and 7 mm and a greatest cross-sectional area of between 0.03 mm^2 and 0.2 mm^2, which length is at least 4 times a square root of the greatest cross-sectional area of the post; and
an implant-restraining element coupled to the post of the implant-receiving element, the implant-restraining element being configured to restrain the implant from separating from the implant-receiving element; and
a cord removably couplable to the tissue anchor, the cord being configured to facilitate passage of the implant therealong and toward the tissue anchor.

17. The apparatus according to claim 16, wherein the cord passes through a portion of the implant-receiving element.

18. The apparatus according to claim 16, wherein the length of the post is at least 5 times the square root of the greatest cross-sectional area of the post.

19. The apparatus according to claim 16, wherein the length of the post is at least 8 times the square root of the greatest cross-sectional area of the post.

20. The apparatus according to claim 16, wherein the length of the post is at least 10 times the square root of the greatest cross-sectional area of the post.

21. The apparatus according to claim 16, wherein the length of the post is at least 15 times the square root of the greatest cross-sectional area of the post.

22. The apparatus according to claim 16, wherein the implant-restraining element is coupled to the post within 2 mm of a proximal end of the post.

23. The apparatus according to claim 22, wherein the implant-restraining element is shaped so as to define an opening therethrough, through which the cord is configured to pass.

24. The apparatus according to claim 22, wherein the implant-restraining element has a greatest cross-sectional area that is at least 1.5 times the greatest cross-sectional area of the post.

25. The apparatus according to claim 24, further comprising a lock configured to be advanced toward the anchor and disposed between the implant and the implant-restraining element, the lock comprising:
a distal portion configured to rest against the implant; and
an expandable proximal portion having a cross-sectional area during a resting state of the lock that is larger than the greatest cross-sectional area of the post and smaller than the greatest cross-sectional area of the implant-restraining element.

26. Apparatus, comprising:
an implant configured to be coupled to cardiac tissue of a patient, the implant comprising:
a spool coupled to the implant; and
a flexible contracting member that is coupled to the spool and the sleeve, such that winding the contracting member around the spool tightens the contracting member; and
a tissue anchor comprising:
a distal tissue coupling element configured to couple the tissue anchor to the cardiac tissue of the patient; and
a proximal implant-receiving element configured to receive at least a portion of the implant and facilitate coupling of the implant to the tissue anchor, the proximal implant-receiving element comprising:
an implant-restraining element coupled to a portion of the implant-receiving element, the implant-restraining element being configured to restrain the implant from separating from the implant-receiving element.

27. The apparatus according to claim 26, wherein the implant comprises an annuloplasty device.

* * * * *